United States Patent [19]

Wenger

[11] 4,396,542

[45] Aug. 2, 1983

[54] METHOD FOR THE TOTAL SYNTHESIS OF CYCLOSPORINS, NOVEL CYCLOSPORINS AND NOVEL INTERMEDIATES AND METHODS FOR THEIR PRODUCTION

[75] Inventor: Roland Wenger, Riehen, Switzerland

[73] Assignee: Sandoz Ltd., Basel, Switzerland

[21] Appl. No.: 299,103

[22] Filed: Sep. 3, 1981

Related U.S. Application Data

[63] Continuation-in-part of Ser. No. 233,713, Feb. 12, 1981.

[51] Int. Cl.$^3$ .............................................. C07C 103/52
[52] U.S. Cl. ............................................. 260/112.5 R
[58] Field of Search .................................. 260/112.5 R

[56] References Cited

U.S. PATENT DOCUMENTS

| 4,108,985 | 8/1978 | Rüegger et al. | 260/112.5 R |
| 4,117,118 | 9/1978 | Harri et al. | 260/112.5 R |
| 4,210,581 | 7/1980 | Rüegger et al. | 424/177 |
| 4,220,641 | 9/1980 | Traber et al. | 260/112.5 R |
| 4,288,431 | 9/1981 | Traber et al. | 424/177 |

FOREIGN PATENT DOCUMENTS 1491509  11/1977  United Kingdom .

OTHER PUBLICATIONS

Mori et al., *Tetrahedron*, vol. 86, pp. 87–90 (1980).
Ko Sawai et al., *Agric. Biol. Chem.*, 45(5), pp. 1223–1228, (1981).

*Primary Examiner*—Delbert R. Phillips
*Attorney, Agent, or Firm*—Gerald D. Sharkin; Robert S. Honor; Thomas O. McGovern

[57] ABSTRACT

A method for the total synthesis of cyclosporins, in particular Cyclosporin A, cyclosporins produced in accordance with the method of the invention and novel intermediates, in particular novel [1S, 2R, 3R]- and [1R, 2S, 3S]-1-nitrilo-1-carbonyl-3-methyl-2-oxy-heptanes and -hept-5-enes, employed in the method of the invention.

17 Claims, No Drawings

METHOD FOR THE TOTAL SYNTHESIS OF CYCLOSPORINS, NOVEL CYCLOSPORINS AND NOVEL INTERMEDIATES AND METHODS FOR THEIR PRODUCTION

The present application is a continuation-in-part of my pending application Ser. No. 233,713 filed Feb. 12th, 1981.

The present invention relates to a method for the total synthesis of cyclosporins, in particular of cyclosporin A and derivatives thereof. The invention also relates to cyclosporins which are produced in accordance with the method of the invention as well as to novel intermediates, in particular novel amino acids, employed in the method of the invention.

The cyclosporins comprise a class of structurally distinctive cyclic, poly-N-methylated undecapeptides having valuable pharmacological, e.g. immunosuppressive and anti-inflammatory activity. They include e.g. cyclosporins A, B, C, D and G as well as corresponding dihydrocyclosporins described for example in U.S. Pat. Nos. 4,117,118; 4,210,581 and 4,108,985 and in DOS Nos. 28 19 094 and 29 41 080. Of these, cyclosporin A in particular has received very considerable attention on account of its outstanding immunosuppressive properties and its usefulness in preventing rejection in a variety of organ transplant operations has been widely reported. Some indication of the very considerable degree of interest which this compound has attracted may be had e.g. from the following publications: "Transplant Proceedings" 12, 2 (1980) pp. 233-293—"Symposium on Pharmacological Immunosuppression in Organ Transplantation"; R. Y. Calne, "Nephron" 26 (1980) pp. 57–63—"Cyclosporin"; R. Y. Calne "Trends in Pharmacological Sciences: Immunosuppression in Clinical Organ Grafting" 1 (1979) pp. 21 and 22; and J. F. Borel "Trends in Pharmacological Sciences etc . . . " 1 (1980) pp. 146-149.

The chemical structure of the cyclosporins is known. The pioneer-work on structure analysis was carried out by Rüegger et al., using physical and degradative analytic techniques with cyclosporin-, dihydrocyclosporin- and iso-cyclosporin-A as substrate. This work is published in detail in "Helv. Chim. Acta" 59, 4 (1976) No. 112, pp. 1075–1092.

The presence of a hitherto unknown amino acid residue, referred to on the basis of its carbon atom content as "the $C_9$-amino acid", was recognised early on. Attempts to isolate the $C_9$-amino acid in free form were unsuccessful. It was however possible to ascribe a basic structure to the $C_9$-amino acid on the basis of derivatives and artefacts obtained on hydrolysis of cyclosporin A and dihydrocyclosporin A, e.g. by hydrolysis of dihydrocyclosporin A followed by esterification and acylation in accordance with the method Dabre and Islam. The methods and results are reported in full in the afforementioned "Helv. Chim. Acta" article.

Attempts to open the cyclosporin A ring system were unsuccessful. Hydrolysis using anhydrous trifluoroacetic acid led, even under mild conditions, to the formation of a mixture of many peptide fragments from which individual peptide fragments could not be fully or effectively isolated.

The basic sequential analysis for cyclosporin A was conducted using a modified Edman degradation procedure with iso-cyclosporin A, which contains a labile, non-peptide linkage at the $C_9$-amino acid, as substrate. Degradation commences with a splitting off of the $C_9$-amino acid in the form of a di-hydro-methylthiohydantoin artefact simultaneous to cleavage of the labile linkage and opening of the peptide cycle.

The absolute configuration for the $C_9$-amino acid was finally determined by x-ray analysis of a further cyclosporin A derivative obtained by reaction with $I_2$ and Thallium-(I)-acetate in accordance with the method of Cambie et al. The $C_9$-amino acid is now identified as [2S,3R,4R,6E]-3-hydroxy-4-methyl-2-methylamino-6-octenoic acid for cyclosporin A and [2S,3R,4R]-3-hydroxy-4-methyl-2-methylamino-6-octanoic acid for dihydrocyclosporin A.

From the foregoing it will be apparent that though the structures of the $C_9$-amino acid and its dihydro derivative are known, the compounds as such are not. They have never been isolated nor produced in isolable form. Nor until now has any method for the synthesis of these acids, nor any method by which they might be obtained in stereochemically pure or substantially pure form ever been described.

Hitherto the cyclosporins have been obtained primarily by microbiological techniques, i.e. as fermentation products e.g. of the fungal strain Tolypocladium inflatum gams [previously known as Trichoderma polysporum (Link ex Pers.)]. Full details of these methods are reported in the literature. Limited chemical modification of the naturally occurring cyclosporins, e.g. cyclosporins A, B, C, D and G is possible and has lead to the development of the corresponding dihydro- and iso-derivatives. Hitherto however reliance has had to be placed entirely on microbiological and semi-synthetic techniques both for the production of cyclosporins and for the preparation of novel cyclosporin derivatives. Inevitably this has placed severe limitations on the further development of a field of research of immediate scientific importance and of major public benefit.

The absence of a totally synthetic method for the production of cyclosporins has been attributable to three basic factors. First there is the problem of the $C_9$-amino acid itself, with its three optically active centres, and the need to find a synthetic route by which this might be obtained in stereochemically pure form. Secondly there is the complex poly-N-methylated structure of the cyclosporin molecule. As is well-known in the art, although numerous methods are available for peptide synthesis, linkage of N-methylated amino acids, in accordance with standard techniques generally results in low yields and epimerisation of the participating N-methylated reactant. This leads to the formation of mixtures of individual optically active peptide isomers. Clearly, when synthesis involves linkage of several N-methylated amino acid moieties the number of diastereoisomers obtained rapidly increases. Isolation of individual isomers, e.g. by column or thin-layer chromatography, becomes an excessively laborious or even virtually impossible task and the resultant product will generally contain a high percentage of impurities. To obtain a cyclosporin in substantially pure form and corresponding in all respects to the natural product has required the formulation of an appropriate and rigorous synthetic strategy by means of which the basic cyclosporin structure may be first obtained in optically pure open-chain form.

Lastly, there is the problem of the final cyclisation step. Even supposing it were possible to obtain the required cyclosporin structure in open-chain form it was not evident that a cyclisation might be achieved without loss of essential, in particular stereochemical, identity. In accordance with the present invention this problem has been met by choice of position at which cyclisation is effected. This choice appears to be critical. As hereinafter discussed the selection of reaction conditions also appears to be important if final yields are to be maintained.

The present invention provides a method for the synthesis of [2S,3R,4R,6E]-3-hydroxy-4-methyl-2-methylamino-6-octenoic acid and [2S,3R,4R]-3-hydroxy-4-methyl-2-methylamino-octanoic acid, and a limited class of derivatives, including the corresponding [2R,3S,4S]-enantiomers in both free and in protected and/or activated form. The product isomers are stereochemically substantially pure. It also provides a method, in particular a synthetic methodic or strategy, for the total synthesis of cyclosporins, in particular cyclosporin A, employing these novel amino acids as starting materials. These methods are described below, and for the specific compound cyclosporin A, in detail, in the accompanying examples. It may here be emphasized that the cyclosporin A produced in accordance with the method of the invention is identical to the isolated natural product.

From the foregoing discussion it will be apparent that in addition to developing an alternative to known microbiological and semi-synthetic techniques for cyclosporin production the present invention opens the way to the preparation of a new generation of cyclosporins, cyclosporin derivatives, and compounds having cyclosporin-like activity. Such derivatives may be obtained by substitution of the novel $C_9$-amino acids of the invention for the $C_9$-amino acids present in known, natural cyclosporins, or by modification of the basic peptide sequence around the cyclosporin chain, in analogy with the development of other known natural-peptide analogues. Further alternatives for possible derivatisation of the basic cyclosporin molecule will be apparent to the skilled worker. Having regard to the existing interest in the cyclosporins as pharmacologically active agents, the implications are apparent.

I. CYCLOSPORIN TOTAL-SYNTHESIS

In general, peptides may be built up synthetically by any appropriate synthetic pathway and choice of pathway is commonly dictated by considerations of simplicity and economy, e.g. by the number of reaction steps required. The most usual approach is to join together smaller peptide units having the appropriate partial sequences. For cyclosporins, e.g. cyclosporin A, it appears that the choice of synthetic pathway is limited. A primary limitation is of course imposed by the choice of position at which cyclisation is to be effected. It also appears however that there are restrictions in the choice of synthetic sequence for obtaining the cyclosporin in open-chain form. The present invention provides a particular strategy for the synthesis of the required open-chain form, which is employed in conjunction with a choice of highly specific reaction conditions for each synthetic step.

The synthetic strategy developed for the preparation of the open-chain form is represented diagrammatically for Cylclosporin A in flow-chart (1A). (In this flow-chart the $C_9$-amino acid residue is designated as occupying position 1 of the product cyclosporin and the remaining residues of the molecule are numbered from this clock-wise and in sequence. In accordance with standard practice all residue sequences represented herein commence with the N-terminal residue). This strategy may be identified as comprising the following main steps:

1. Preparation of a tetrapeptide having the sequence 4 through 7, commencing with 7 and proceeding by successive linkage of the residues 6, 5 and 4 to the N-terminal;
2. Preparation of a dipeptide having the sequence 2–3 and linkage of this to the N-terminal of the tetrapeptide obtained via step 1, to obtain a hexapeptide having the sequence 2 through 7;
3. Linkage of the $C_9$-amino acid to the N-terminal of the hexapeptide obtained via step 2, to obtain a heptapeptide having the sequence 1 through 7; and
4. Preparation of a tetrapeptide having the sequence 8 through 11 and linkage of this to the N terminal of the heptapeptide obtained via step 3 to obtain a linear endecapeptide having the sequence 8 through 7.

In order to ensure that chirality of the $C_9$-amino acid is maintained at step 3, this is preferably introduced in a form having a protecting group bridging the 2-N and 3-O functions and completing a six- or, more preferably, five-membered ring system, such as hereinafter described in relation to formula III, in particular as described in example 1k.

It will be seen that this strategy proceeds essentially via a step-wise elongation of the peptide chain starting from the chosen C-terminal residue 7. The choice of reaction conditions for each step in the synthesis, in particular the choice of temperature and base, is important. Using the particular conditions described in examples 1a to s for each step in the synthesis, it has been found that the problem of epimerisation hereinbefore discussed is largely overcome and that reaction proceeds with the production of the desired isomer in substantially pure form, i.e. substantially free from epimerisation products. The desired isomer is isolated from the reaction medium in good yield, employing a single chromatographic run. In this latter connection it is particularly to be noted that, for the synthesis here described, when mixed anhydride carboxy activating groups are employed, epimerisation is, in a number of instances, minimalised by the use of relatively strong bases such as triethylamine and ethyldiisopropylamine, and by the avoidance of weaker bases such as N-methylmorpholine and pyridine. Data from the literature suggests that the reverse would be true.

The final cyclisation may be performed by reaction of an obtained, linear endecapeptide having the desired sequence, in free-N and carboxy-activited form (i.e. having an activating group at the C-terminal and a free-amino group at the N-terminal). Suitably the reaction is conducted in the presence of a base. The choice of reaction temperature will of course depend on the particular carboxy-activating group selected but this will generally be in the range of from −20° to 30° C. Suitable bases include e.g. ethyldiisopropylamine and N-methylmorpholine. Suitable carboxy-activated forms include e.g. the carbonylazide and, preferably the activated-ester forming on reaction with benzotriazol-1-yl-oxy-tris(dimethylamino)-phosphonium-hexafluorophosphate [also known as Castro-reagent], herein referred to as the "Castro-ester".

Carbonylazides may be prepared directly from an obtained linear endecapeptide in free-N and free-carboxy form, e.g. by reaction with diphenylphosphonic acid azide in the presence of dimethyl formamide and a base such as triethylamine. The reaction is conveniently carried out at a temperature of from −10° to 30° C. and proceeds directly with concurrent cyclisation.

Carbonylazides may also be prepared from an obtained linear endecapeptide in free-N or N-protected, e.g. in N-Boc-protected and carboxy-ester-protected, e.g. carboxy-$C_{1-4}$ alkyl- or carboxy-benzyl-ester-protected form, by a process comprising:

(i) reaction of the carboxy-ester-protected endecapeptide in free-N or N-protected form with hydrazine hydrate, optionally dissolved in dimethylformamide, at a temperature of from e.g. 0° to 30° C., (ii) removal, when required, of the N-protecting group, e.g. removal of an N-Boc-protecting group by acid treatment, e.g. in the presence of trifluoroacetic acid, at a temperature of e.g. ca. 0° C. and (iii) oxidation of the obtained hydrazide, e.g. by treatment with t-butylnitrite in the presence of an acid such as HCl (to prevent oxidation of the now unprotected amino group) at a temperature of from e.g. −20° to 0° C.

Final cyclisation of the carbonylazide is thereafter effected by addition of a base, such as triethylamine or ethyldiisopropylamine and at a temperature of e.g. −20° to 0° C.

Cyclisation in accordance with the carbonylazide method is represented in the last 3 steps of accompanying flow-chart (1A) and is exemplified in the following examples 1t through 1v.

"Castro-esters" may be prepared from an obtained linear endecapeptide in free-N and free-carboxy form by reaction with benzotriazol-1-yl-oxy-tris(dimethylamino)-phosphonium hexafluorophosphate in the presence of a base such as triethylamine or N-methyl-morpholine, at a temperature of from e.g. −20° to 30° C., in an inert solvent such as chloroform or methylene chloride. The reaction proceeds with concurrent cyclisation. Cyclisation in accordance with this second method is represented in accompanying flow-chart (1B) and is exemplified in the following examples 1w through 1y.

Using the carbonylazide as carboxy activated form under the reaction conditions herein described in Example 1v, the formation of side products is not avoided, and the yield of Cyclosporin A at the final cyclisation is low. However, the indicated reaction parameters for this method are in general appropriate and Cyclosporin A, which is identical with the naturally occurring product, may be recovered from the obtained reaction medium in substantially pure form. The yield of Cyclosporin A may be increased by appropriate and routine adjustment of the reaction conditions described in Example 1v, e.g. by adjustment of the ratios of participating reactants and choice of solvent medium and by the close control of reaction temperature and of pH.

Use of the "Castro-ester" as carboxy activated form under the reaction conditions of Example 1y however leads to the formation of substantially higher amounts of Cyclosporin A. Again the product Cyclosporin A is identical to the naturally occurring product and may be isolated from the reaction medium in pure form and in good yield. The use of the "Castro-ester" for the cyclisation step in accordance with the method of Example 1y is accordingly preferred.

For the purposes of the cyclisation reaction the peptide may, if desired, be in O-protected form, i.e. may bear an O-protecting group, such as hereinafter described, at the $C_9$-amino acid residue and/or, in the case of Cyclosporin C or derivatives thereof, at the 2-threo-nine residue. Such O-protecting groups are then removed subsequent to ring-closure by methods known in the art, e.g. (i), for the removal of alkyl groups, such as t-butyl, by treatment with an acid such as trifluoroacetic acid or HCl in a solvent medium such as methanol/water at a temperature of from −20° to 30° C., or (ii), for the removal of ester groups, such as acetyl, by hydrolysis in the presence of an alcoholic alkali metal- or alkaline-earth metal-alcoholate, again at a temperature of from 0° to 30° C., or (iii), for the removal of a benzyl group, by hydrogenation in the presence of a metal catalyst such as palladium on charcoal, in an inert solvent such as ethanol, at a temperature of from 0° to 30° C. or by treatment with sodium in liquid ammonia at a temperature of −35° C.

When hydrogenation according to method (iii) above is employed, and the $C_9$-amino acid moiety of the endecapeptide contains a double-bond, the double-bond is simultaneously reduced to yield the corresponding dihydro-cyclosporin as end-product. Initially obtained cyclosporins containing an unsaturated $C_9$-amino acid residue may in any case be converted into the corresponding dihydro cyclosporin derivative by reduction, e.g. in accordance with the methods known and described in the art for reducing naturally occurring cyclosporins, e.g. cyclosporins C and D, for example by catalytic hydrogenation, e.g. in accordance with the general methods disclosed in U.K. Patent Specification No. 1,567,201. Reduction is suitably effected under neutral pH conditions at a temperature of from 20° to 30° C. and at atmospheric or slightly elevated pressure, in the presence of a catalyst such as platinum and, preferably, palladium (e.g. palladium on charcoal) in the presence of an inert solvent or diluent, such as ethyl acetate. Flow-charts (1A) and (1B) represent the total synthetic pathway for producing Cyclosporin A. It will, however, be appreciated that the same basic strategy may be applied to obtain other cyclosporins and cyclosporin derivatives, e.g. by substituting threonine, valine or norvaline residues for the α-amino-butyric acid residue at the 2-position, to obtain Cyclosporins C, D and G or by replacement of the (2S,3R,4R,6E)-3-hydroxy-4-methyl-2-methyl-amino-oct-6-enoic acid residue at the 1-position with derivatives thereof as described herein.

SYNTHESIS OF THE $C_9$-AMINO ACID

The method of the invention for the synthesis of the $C_9$-amino acid in stereochemically pure form is represented diagrammatically in the accompanying flow-chart (2). The individual steps in the synthesis may be carried out as follows:

(a) Etherification to introduce O-protecting $C_{1-4}$-alkyl or $C_{7-11}$aralkyl groups X' and X" (formula XVII). Preferably X' and X" are the same. The etherfication may be performed by reaction of the compound of formula XVIII with alkyl- or aralkyl-halides, for example a benzyl halide, in particular benzyl bromide, suitably in the presence of a condensation agent, e.g. in the presence of an alkali metal hydroxide, in particular potassium hydroxide. The reaction is preferably performed under anhydrous conditions at a temperature of from e.g. 20° to 100° C. Starting materials of formula XVIII are known (see e.g. J. Chem. Soc., Chem. Commun. 1975, (20) pp. 833–835) and may be produced by known methods.

(b) Reaction with N-chloro- [Hal=Cl] or N-bromo- [Hal=Br] -Succinimide at a temperature of e.g. −10° to 30° C. The reaction is preferably carried out in the dark using carbon tetrachloride as solvent medium Compounds of formula XVII are known (J. Chem. Soc., Supra).

(c) Hydrolysis and epoxidation, e.g. in the presence of an aqueous alkali, in particular an aqueous alkali metal hydroxide, in particular potassium hydroxide. The reaction is suitably conducted at a temperature of from 20° to 60° C.

(d) Methylation to effect opening of the epoxy ring. This step may be effected by reaction of the compound of formula XV with methyl lithium in the presence of a cuprous salt, in particular a cuprous halide, e.g. cuprous iodide, at reduced temperature. Conveniently the methyl lithium and the cuprous salt are added at a temperature of from $-20°$ to $0°$ C. and the reaction mixture then further cooled to $-60°$ to $-20°$ C.

(e) Ether cleavage to remove protecting groups $X'$ and $X''$. When $X'$ and $X''$ are aralkyl, cleavage may be effected reductively, e.g. by catalytic hydrogenation for example using 10% palladium/charcoal as catalyst, at a temperature of from 0° to 30° C. and at normal or slightly elevated pressure. When $X'$ and $X''$ s.- or t.-alkyl, cleavage is effected hydrolytically, e.g. in the presence of trifluoroacetic or hydrochloric acid, again at a temperature of from e.g. 0° to 30° C.

(f) Introduction of a protecting group $(R_3)_2C<$ wherein $R_3$ = methyl or ethyl, e.g. by reaction of a compound of formula XIII with acetone or 2,2-dimethoxy-propane (to produce a compound of formula XII wherein $R_3 = CH_3$), or with di-ethyl ketone, (to produce a compound of formula XII wherein $R_3 = C_2H_5$). The reaction is effected in an acid medium, e.g. in the presence of p-toluenesulfonic acid at elevated temperature, e.g. at 40° C. to reflux.

(g) Tosylation e.g. by reaction with a tolyl-, in particular p-tolyl-sulfonyl halide, e.g. p-toluenesulfonyl chloride, to produce a compound of formula XI wherein $R_4$ = tolyl, in particular p-tolyl. The reaction is carried out in the presence of an organic base such as pyridine, at a temperature of from e.g. $-20°$ to $20°$ C.

(h) Reaction with an alkali metal cyanide, in particular potassium cyanide, under anhydrous conditions. The reaction is preferably carried out using dimethyl-sulfoxide as solvent, and is suitably performed under an inert atmosphere. The reaction proceeds best at elevated or slightly elevated temperatures of e.g. from 20° to 70° C.

(i) Reduction and hydrolysis, e.g. using diisobutylaluminium hydride in the presence of an aprotic solvent such as tetrahydrofuran, hexane or toluene. The reaction is preferably carried out at a temperature of from $-80°$ to $-20°$ C. under an inert atmosphere.

(j) Condensation with n-butyllithium, e.g. in the presence of ethyltriphenylphosphonium bromide or analogues thereof having 3 to 5 carbon atoms in the alkyl moiety, or in the presence of ethyltriphenylphosphonium bromide in accordance with the method described by Schlosser [Ann. Chem. 708, 1 (1967)]. The reaction is suitably carried out in an aprotic solvent or diluent such as tetrahydrofuran and/or ether. When conducted at a temperature of ca. $-90°$ to $-30°$ C. in the presence of t-butanol, the reaction leads to products of formula VIII in trans-form. When the reaction is carried out at ambient temperatures, e.g. of from 0° to 30° C. in the absence of t-butanol, the corresponding cis-form is obtained.

(k) Removal of the protecting group $(R_3)_2C<$ e.g. by hydrolysis e.g. in the presence of a dilute aqueous mineral acid such as hydrochloric acid. The reaction is suitably performed at a temperature of from 0° to 30° C.

(l) Introduction of an O-protecting group $X_3$, e.g. a 1-methoxyethyl, 1-ethoxyethyl or 2-methoxyisopropyl group. The reaction is conveniently carried out by means of a three-step procedure comprising: (i) esterification, in particular benzoylation, of the primary alcohol function, e.g. by reaction with a benzoyl halide, especially benzoyl chloride in the presence of a weak organic base, in particular pyridine, (ii) ketalisation of the secondary alcohol function, e.g. by reaction with a $(C_{1-4}alkoxy)$-vinyl ether, for example ethoxy-vinyl ether, in the presence of a catalytic amount of an acid, in particular an organic acid such as trifluoroacetic acid and (iii) hydrolysis, e.g. in the presence of an aqueous base such as sodium hydroxide, with removal of the protecting benzoyl group at the primary alcohol function. The reaction sequence (i)→(ii)→(iii) is conveniently carried out at a temperature of from 0° to 30° C.

(m and m') Oxidation, e.g. in accordance with the method described by Moffat [J.A.C.S. 87, 5661 (1965) and 88, 1762 (1966)] in the presence of dimethylsulfoxide and dicyclohexylcarbodiimide with the addition of pyridine and trifluoroacetic acid. The reaction is suitably performed at a temperature of from 0° to 30° C.

(n and n') The reaction corresponds to the first step of a Strecker synthesis and may be effected by reaction with HCN or, preferably, an alkali metal cyanide, in particular KCN, and ammonia or ammonium chloride (to produce compounds of formula Va or Vb wherein $R_1 = H$) or methylamine (to produce compounds of formula Va or Vb wherein $R_1 = CH_3$). The reaction is suitably performed at a temperature of from 0° to 30° C.

(l' and l'') Removal of O-protecting group $X_3$ e.g. by deketalisation in the presence of an acid such as trifluoroacetic acid, and dicyclohexylcarbodiimide at a temperature of from 0° to 30° C.

Although it is possible to proceed directly from the compound of formula VIIa to Va via steps m and n, without introduction of protecting group $X_3$ (formulae VIIb through Vb), synthesis via steps l, m', n' and l'' is preferred.

(o) Introduction of a protecting group $(X_2+X_3)$, completing a B 6- or, preferably 5-membered ring system, e.g. by reaction of a compound of formula Va with acetone or 2,2-dimethoxy-propane [to produce a compound of formula IV wherein $(X_2+X_3)=(CH_3)_2C<$] or with carbonyl or thiocarbonyl-diimidazole or with phosgene [to produce a compound of formula IV wherein $(X_2+X_3) = $ -CO- or -CS-]. The reaction is preferably carried out in the presence of methylene chloride or toluene as solvent or diluent and at a temperature of e.g. 0° to 30° C.

(p and p') Selective hydrolysis and isomerisation, e.g. in an aqueous alkali medium such as aqueous sodium hydroxide [to yield the free acids of formula (IIIb$^1$)—process step p] or in the presence of, successively, an alcoholic alkali metal- or alkaline-earth- metal-alcoholate or -carbonate suspension and an acid, e.g. HCl [to yield esters of formula (IIIa$^1$)—process step p']. By variation of the alcoholic component, compounds of formula IIIa$^1$ may be obtained wherein $R_5 = C_{1-4}$alkyl. Preferably the reaction is carried out employing an ethanolic sodium- or potassium-carbonate suspension to obtain compounds of formula (IIIa$^1$) wherein $R_5 = C_2H_5$. Thermodynamically the reaction proceeds such that the carbonyl group assumes the trans-position relative to the adjacent alkyl substituent Z-CH(CH₃)-. Conveniently the reaction is carried out at a temperature of from 0° to 20° C.

(q and q') Hydrogenation, e.g. catalytic hydrogenation, for example employing a palladium/charcoal catalyst at a temperature of from e.g. −5° to 40° C. under normal or at slightly elevated pressure. Inclusion of step q or q' leads to product amino acids of formula II wherein -x-y-=-CH₂-CH₂-. Although as shown in flow-chart (2), hydrogenation is conveniently carried out subsequent to step p or p', it will be appreciated that it is equally possible to effect hydrogenation subsequent to any of steps j through o. Clearly, hydrogenation at an earlier phase in the reaction sequence may be employed to produce the corresponding compounds of formulae VIII through IV wherein the group CH₃-CH=CH-CH₂- (=Z) is replaced by the group CH₃-CH₂-CH₂-CH₂-.

(r) Selective hydrolysis, e.g. in the presence of an aqueous alkali metal- or alkaline-earth metal-hydroxide in particular NaOH or KOH. The reaction is suitably performed at a temperature of from 0° to 20° C. The initially obtained salt may be converted into the free acid of formula IIIb¹ or IIIb², e.g. by addition of a dilute mineral acid such as HCl. At pH 6-7 the free acids precipitate out and may readily be recovered from the reaction medium in pure form.

(s) Removal of protecting group (X₂+X₃). When (X₂+X₃) is e.g. carbonyl or thiocarbonyl, removal is conveniently effected by alkaline hydrolysis, e.g. in the presence of an aqueous alkali metal or alkaline-earth metal hydroxide, analogously to step r, at a temperature of from e.g. 40° to 70° C. When (X₂+X₃) is e.g. a group of formula (CH₃)₂C<, removal is effected by acid hydrolysis, e.g. in the presence of a dilute mineral acid such as HCl, at a temperature of from 10° to 40° C.

The initially obtained salt, e.g. in the case of acid hydrolysis, the initially obtained acid addition salt, may be converted into the free amino acid by adjustment to ca. pH 6-7, by addition of an appropriate amount of an alkali or, analogously to step r, of an acid. At the isoelectric point the free amino-acids precipitate out and may be recovered from the reaction medium in substantially pure form.

Each of the above reaction steps a to s is suitably carried out in the presence of an inert solvent or diluent. Unless otherwise specified, this may be any appropriate solvent or diluent which is inert to the reaction components under the selected reaction conditions. Suitable solvents and diluents are illustrated in the accompanying examples.

Starting from compounds of formula XVIII wherein the asymmetric carbon atoms both have the S-configuration, amino acids of formula II are obtained, wherein the positions 2, 3 and 4 have the configuration S, R and R respectively. The enantiomers wherein the positions 2, 3 and 4 have the configuration R, S and S respectively are obtained starting from compounds of formula XVIII wherein the asymmetric carbon atoms both have the R-configuration.

For synthetic use, the amino acids of formula II will generally be employed in protected and/or activated form, e.g. as hereinafter described. Such forms may be obtained by methods known in the art. Particular methods for the synthesis of the free acids of formula II, and their salts, as well as protected or activated forms thereof are described in the accompanying examples 2 through 10.

In accordance with the foregoing the present invention provides, in a first aspect, a process for the production of a cyclosporin of formula I,

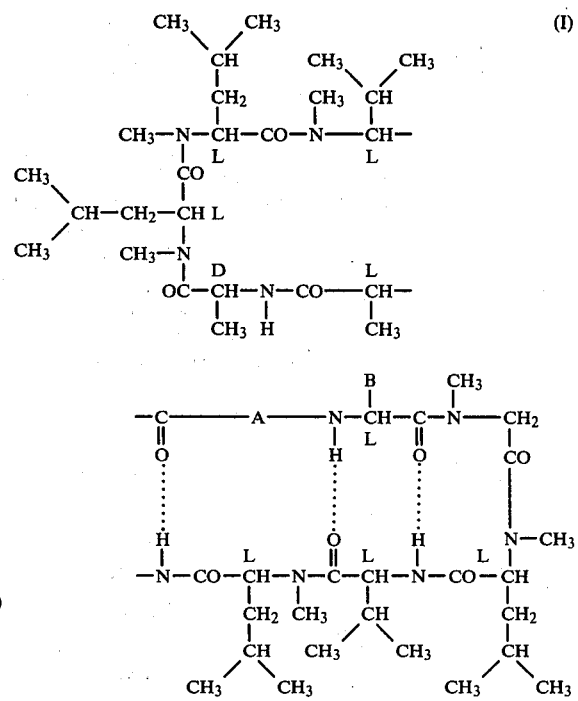

wherein A is a residue of formula Ia,

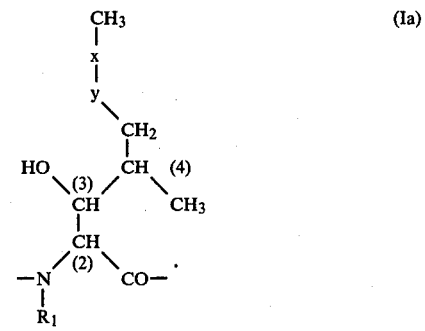

wherein R₁ is hydrogen or methyl and -x-y- is -CH₂-CH₂- or -CH=CH- and the positions 2, 3 and 4 have the configuration S,R and R or R,S and S respectively, and B is ethyl, 1-hydroxyethyl, isopropyl or n-propyl, which process comprises (a) removing the O-protecting group(s) from a cyclosporin of formula I in O-protected form;

(b) cyclising a straight-chain endecapeptide having the sequence indicated in formula I, commencing with H-(D)-Ala- as N-terminal and terminating with -Ala-OH as C-terminal, in unprotected or O-protected form and, when required, carrying out process step (a); and, when desired, (c) hydrogenating a cyclosporin of formula I thus obtained wherein -x-y- is -CH=CH- to obtain the corresponding cyclosporin wherein -x-y- is -CH₂-CH₂-.

The invention also provides cyclosporins of formula I whenever prepared by the process defined above, as well as "synthetic" cyclosporins of formula I in general.

[The word "synthetic" as used herein in relation to compounds of the invention, e.g. in relation to cyclosporins of formula I above, means compounds obtained essentially by techniques used in the art of synthetic chemistry. It excludes natural products and products obtained by biological techniques, as well as synthetic derivatives obtained from, e.g. obtained by chemical modification or degradation, of biologically obtained cyclosporins.]

In a further aspect the present invention also provides a cyclosporin of formula I obtained from a compound of formula II as hereinafter defined in free or in protected and/or activated form, e.g. produced from a compound of formula II in free or in protected and/or activated form via chemical reaction.

Cyclosporins of formula I above, wherein A is a residue of formula Ia as defined, with the proviso that, when $R_1$ is methyl and -x-y- is $-CH_2-CH_2-$ or trans $-CH=CH-$ the positions 2, 3 and 4 have the configuration R,S and S respectively are novel compounds and are claimed per se.

As previously indicated, although the basic structure as well as the absolute configuration of two of the compounds of formula II of flow-chart (2), namely the [2S,3R,4R]-3-hydroxy-4-methyl-2-methylamino-octanoic and -[6E]-octenoic acids, have previously been determined and described, these compounds, like the other compounds of formula II, are novel. They have not previously been known in isolated or in isolable form nor have they ever previously been synthesised, nor has any method for their synthesis in stereochemically pure form ever previously been disclosed.

It will moreover readily be appreciated that apart from their value as intermediates in the total synthesis of cyclosporins, in particular cyclosporin A and derivatives thereof, as novel amino acids, the compounds of formula II, together with their activted and protected forms, for example the compounds of formula IIIb[1] and IIIb[2] shown in flow-chart (2), are of broad utility and significance in the synthesis of novel cyclic and acylic chemical entities in general, and of novel peptides, i.e. di- and polypeptides, in particular. The compounds of formula II, together with novel derivatives thereof, for example their protected and activated forms, and the acyclic peptide intermediates herein described, therefore also comprise a part of the invention.

In a further aspect the invention accordingly provides:

(A) A synthesis [1S,2R,3R]- or [1R,2S,3S]-1-nitrilo-1-carbonyl-3-methyl-2-oxy-heptane or -hept-5-ene. [The word "synthetic" in the above definition has the meaning previously given.

The word "nitrilo" as used throughout the present specification and claims means a tervalent nitrogen atom, i.e. a radical of formula >N-.

The words "imino" and "methylimino" mean divalent nitrogen containing radicals of the formula -NH- and -N($CH_3$)- respectively. "Carbonyl" means a radical of formula >C=O and "oxy" a radical of formula -O-.

It will be understood that one valency of each of the above defined radicals attaches to the defined heptane or hept-5-ene moiety at the position indicated.]

In that compounds defined under (A) above having a 1-carboxy radical in free, protected or activated form or a 1-amino or 1-methyl amino radical in free or protected form, as the free amino acids of formula II, are in themselves novel entities, never previously described, synthesised or obtained in isolated or isolable form, the present invention also provides:

(B) A [1S,2R,3R]- or [1R,2S,3S]-1-nitrilo-1-carboxy-3-methyl-2-oxy-heptane or -hept-5-ene in free or in carboxy-protected or -activated form; as well as (C) A [1S,2R,3R]- or [1R,2S,3S]-1-amino- or -1-methylamino-1-carbonyl-3-methyl-2-oxy-heptane or -hept-5-ene in free or in N-protected form.

The 2-oxy radical of the compounds defined under (A), (B) and (C) may be e.g. 2-hydroxy. In the compounds defined under (A) and (B) the 1-nitrilo radical may be e.g. a 1-imino or 1-methylimino radical. Such compounds may be obtained synthetically, for example in accordance with the procedures herein described, or known in the art, and may if desired be recovered in pure or substantially pure form. Carboxy- and N-protecting groups which may be present in the defined compounds include, e.g. those hereinafter specifically described. Alternatively the compounds may be in free form.

In a more particular aspect the present invention also provides a compound of formula II,

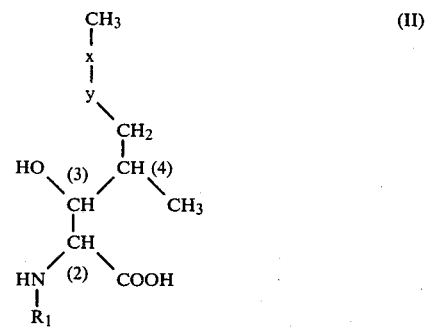

wherein $R_1$ is hydrogen or methyl, -x-y- is $-CH_2-CH_2-$ or $-CH=CH-$ and the positions 2, 3 and 4 have the configuration S,R and R or R,S and S respectively, in free form or in protected and/or activated form.

Compounds of formula II above in free form are the compounds of formula II of flow-chart (2). In accordance with the present invention these compounds may be obtained synthetically by removing protecting groups from a compound of Formula II in protected form. Removal of protecting groups may be effected in accordance with known techniques. Compounds of formula II in free form may in particular be prepared in accordance with the method of process step s or (r+s) of flow-chart (2). The product compounds may be isolated in pure or substantially pure form. Generally for use in synthetic chemistry, e.g. in peptide synthesis, for example as in the total synthesis of cyclosporin A herein described, it will be preferred to use the compounds of formula II in protected and/or activated form, in particular in protected or protected and activated form. Such forms correspond to those of known type and commonly employed in relation to known amino acids, in particular known hydroxy-amino acids such as serine and threonine. Preferably such compounds will be in free- or activated-carboxy and N-protected form or in carboxy-protected and free-N form, the hydroxy group in each case being optionally in O-protected form. Such protected and activated forms include those of the formula III,

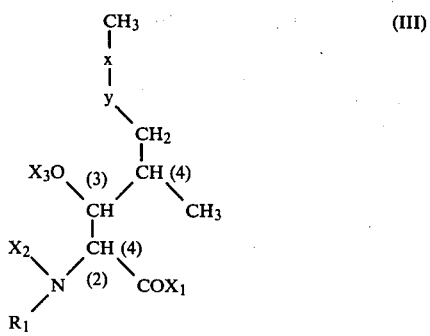

(III)

wherein
-x-y- is -CH$_2$-CH$_2$- or -CH=CH-,
R$_1$ is hydrogen or methyl,
X$_1$ is hydroxy or a carboxy-protecting or -activating group,
X$_2$ is hydrogen or an N-protecting group,
X$_3$ is hydrogen or an O-protecting group, or
(X$_2$+X$_3$) is a protecting group bridging the 2-N and 3-O functions, or
(X$_2$+R$_1$) is a divalent N-protecting group, whereby at least one protecting group is present, and wherein the positions 2, 3 and 4 have the configuration S,R and R or R,S and S respectively.

In accordance with standard synthetic procedures, compounds of formula III will usually be employed, wherein either X$_1$ is hydroxy or a carboxy-activating group and the 2-N function is in N-protected form, or X$_1$ is a carboxy-protecting group and the 2-N function is in free form. Preferred compounds of formula III are accordingly those wherein:

(1a)

R$_1$ is hydrogen or methyl,
X$_1$ is hydroxy or a carboxy-activating group,
X$_2$ is an N-protecting group and
X$_3$ is hydrogen or an O-protecting group, or
(X$_2$+X$_3$) is a protecting group bridging the 2-N and 2-O functions, or
(X$_2$+R$_1$) is a divalent N-protecting group; and especially (1b)

R$_1$ is hydrogen or methyl,
X$_1$ is hydroxy or a carboxy-activating group, and
(X$_2$+X$_3$) is a protecting group bridging the 2-N and 3-O functions; or (2)

R$_1$ is hydrogen or methyl,
X$_1$ is a carboxy-protecting group, and
X$_2$ is hydrogen and
X$_3$ is hydrogen or an O-protecting group.

The use of compounds of formula III wherein both the 2-N and carboxy functions are in protected form may none-the-less be appropriate, for example in circumstances where it is desired to introduce a compound of formula II into a reaction medium in non-reactive pre-cursor form and to remove the carboxy-protecting group or the N-protecting group in situ, e.g. at a particular phase in the reaction procedure.

The intermediates of formulae IIIa$^1$, IIIa$^2$, IIIb$^1$ and IIIb$^2$ of flow chart (2) are themselves protected forms of the formula II compounds, falling within the scope of formula III.

As such the compounds of formulae IIIa$^1$ and IIIa$^2$, and in particular of formula IIIb$^1$ and IIIb$^2$ may be employed directly in the synthesis, e.g. of peptide derivatives, without preparation or recovery of the free amino acids of formula II. The protected and/or activated forms of the compounds of formula II, in particular of formula III, may be prepared, starting from the compounds of formula II in free form, by introducing one or more protecting and/or activating groups, e.g. one or more protecting groups and, optionally, a carboxy-activating group. Thus compounds of formula III are obtained from compounds of formula II in free form by introducing a carboxy-protecting or -activating group X$_1$ and/or either (i) an N-protecting group X$_2$ or (X$_2$+R$_1$) and/or an O-protecting group X$_3$ or (ii) a protecting group (X$_2$+X$_3$) bridging the 2-N and 3-O functions.

The preferred compounds of formula III defined above may be prepared from compounds of formula II in free form either:

(i) by introducing an N-protecting group X$_2$ or (X$_2$+R$_1$) and, optionally an O-protecting group X$_3$ or introducing a protecting group (X$_2$+X$_3$) bridging the 2-N and 3-O functions and, optionally introducing a carboxy-activating group X$_1$; or (ii) by introducing a carboxy-protecting group X$_1$ and, optionally, an O-protecting group X$_3$.

The introduction of protecting and/or activating groups as aforesaid may be carried out in accordance with any of the techniques known and commonly employed in the art of amino-acid and, in particular, peptide chemistry.

The protected and activated forms of the compounds of formula II, in particular of formula III, may also be prepared by selectively removing at least one protecting group from a compound of formula II in protected and, optionally, activated form and containing at least two protecting groups, so as to leave at least one protecting group remaining. Removal, e.g. cleavage, of protecting groups may again be performed in accordance with techniques known in the art, e.g. in accordance with process step r of flow-chart (2).

Compounds of formula III above wherein R$_1$ is hydrogen or methyl, -x-y- is -CH$_2$-CH$_2$- or -CH=CH-, X$_1$ is hydroxy or C$_{1-4}$ alkoxy, (X$_2$+X$_3$) represents a protecting group bridging the 2-N and 3-O functions and completing a 6- or, preferably, 5-membered ring, in particular a carbonyl-, thiocarbonyl or isopropylidene group and the positions 2, 3 and 4 have the configuration R,S and S or S,R and R respectively may also be prepared in accordance with process step p or p' of flow-chart (2), i.e. by selectively hydrolysing and isomerising a compound of formula IV,

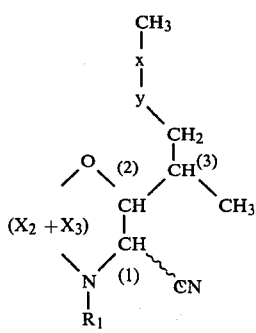

(IV)

wherein $R_1$ and -x-y- have the meanings given above and $(X_2+X_3)$ represents a protecting group as defined above bridging the 1-N and 2-O functions and the positions 2 and 3 have the configuration R and R, or S and S respectively, in an aqueous alkaline medium or in the presence of an alcoholic alkali metal- or alkaline-earth metal-alcoholate. The product compound may be isolated directly from the reaction medium in salt form or in free form on acidifying e.g. with HCl.

Suitable protecting and activating groups are those known in the art, whereby the term "protecting groups" will be understood to mean groups which may conveniently be removed to provide the originally protected group in free form and without affecting the essential identity of the compound protected.

The products of the above processes may be isolated in substantially pure form.

Suitable carboxy-protecting and -activating groups $(X_1)$ include e.g the tertiary butoxy (t-butyl ester); diphenylmethoxy (benzhydryl ester); benzyloxy (benzyl ester); p-methoxybenzyl ester; o-nitrophenyl ester; ethoxy (ethyl ester); 1-hydroxy-benzotriazole ester; N-hydroxy-5-norbornene-2,3-dicarboximide; 3-hydroxy-4-oxo-3,4-dihydro-1,2,3-benzotrianic ester; 8-hydroxyquinoline ester; isobutyl ester; methoxy (methyl ester); p-nitrobenzyl ester; p-nitrophenoxy (p-nitrophenyl ester); phenylazophenyl ester; pentachlorophenyl ester; pentafluorophenyl ester; phenyl ester; p-chlorophenyl ester; 2-benzyloxyphenyl ester; o-methoxyphenyl ester; 4-picolyl ester; pentamethylbenzyl ester; 1-phenyl-3-methyl-4-nitroso-5-(N-benzyloxycarbonylglycyl)-amino-pyrazole ester; 4-methylthiophenyl ester; n-succinimide ester; 2,4,5-trichlorophenyl; 2,4,6-trimethylbenzyl ester; polyethyleneglycol ester; p-nitrophenylthio ester; phenylthiol ester; trimethylsilyl; trimethylsilylethyloxy, and trimethylsilyloxy groups. Further examples of suitable carboxy-activating groups $(X_1)$ include alkoxycarbonyloxy-, (mixed anhydride)-groups, such as e.g. methoxy-, ethoxy- and t.-butyloxycarbonyloxy;alkylcarbonyl groups, such as pivaloylanhydride (trimethylacetylanhydride) and dimethylacetylanhydride; alkylphosphonic acid anhydride groups [such as are described in Angew. Chem. 92 (1980) 129] including n-propylphosphonic acid anhydride; and the azide group.

Suitable N-protecting groups $(X_2)$ include known urethan-type protecting groups such as the adamantyloxycarbonyl; t-amyloxycarbonyl; 2-(p-phenylazophenyl)isopropyloxycarbonyl; 5-benzisoxazolylmethyleneoxycarbonylamino; t-butyloxycarbonyl; 2,2,2-trifluoro-t-butyloxycarbonylaminoethyl; 2-(p-diphenyl)-isopropyloxycarbonyl; 3,5-dimethoxy(α,α-dimethyl)benzyloxycarbonyl; p-dihydroxyborylbenzyloxycarbonylamino; 9-fluorenylmethoxycarbonyl; isobornyloxycarbonyl; 1-methylcyclobutyloxycarbonyl; methylsulfonylethyloxycarbonyl; 2-methylsulfonylethoxycarbonyl; n'-4-picolyloxycarbonyl; piperidino-oxycarbonyl; cyclopentyloxycarbonyl; 2-phenylisopropyloxycarbonyl; p-phenylazobenzyloxycarbonyl; p-tosylaminocarbonyl; β,β,β-trichloroethyloxycarbonyl; benzyloxycarbonyl; p-bromobenzyloxycarbonyl; p-chlorobenzyloxycarbonyl; p-nitrobenzyloxycarbonyl; p-methoxybenzyloxycarbonyl; and 2,2,2-trifluoro-1-benzyloxycarbonylaminoethyl groups as well as the trialkylsilan-type protecting groups such as the trimethylsilan, triethylsilan, tri-n-butylsilan and t.-butyl-dimethylsilan groups.

Further suitable N-protecting groups $(X_2)$ as well as O-protecting groups include e.g. the acetyl; 2,2,2-trifluoro-1-t-butyloxycarbonylaminoethyl; benzoyl; benzyl; α-methyl-α-(5,4-dimethyl-2-phenylazophenoxy)-propionyl; 2,4-dimethoxybenzyl; dinitrophenyl; 1-dimethylaminonaphthalene-5-sulfonyl (dansyl); diphenylphosphinamide; formyl; α-methyl-α-(4-methyl-2-phenylazophenoxy)propionyl; 4,4'-dimethoxybenzhydryl; o-nitrophenylsulphenyl; 2-(4-tolylsulfonyl)ethoxy; pentafluorophenyl; phthalyl; α-picolinyl; 2-pipecolic acid; trichloroacetyl; trifluoroacetyl; tetrafluoropropionyl; tetrahydropyranyl; tosyl; and trityl groups.

Suitable protecting groups bridging the 2-N and 3-O functions $[(X_2+X_3)]$ include the carbonyl, thiocarbonyl and isopropylidene groups. Suitable divalent N-protecting groups $[(X_2+R_1)]$ include the phthalyl group.

As afforesaid the compounds of formula II and, in particular, the protected and/or activated forms thereof, are of general significance and utility in the synthesis of further novel chemical entities. In particular they are indicated for use in the synthesis of peptides, in particular cyclosporin derivatives and intermediates for the preparation thereof, e.g. as hereinbefore indicated. For this purpose the compounds of formula II, or their protected and/or activated forms may if desired be first recovered in pure or substantially pure form prior to further reaction or, where appropriate employed directly in situ in the reaction medium in which they are prepared. Reaction may be effected in accordance with any of the techniques commonly employed in the art of amino acid chemistry and, in particular, of peptide synthesis, or in accordance with the particular techniques hereinbefore described for the synthesis of cyclosporin A and the intermediates and derivatives thereof.

Accordingly in a further aspect the present invention also provides:

(D) A [1S,2R,3R]- or [1R,2S,3S]-1-nitrilo-1-carbonyl-3-methyl-2-oxy heptane or -hept-5-ene, obtained from a compound of formula II, as hereinbefore defined in free or in protected and/or activated form, e.g. produced by derivatisation of a compound of formula II, i.e. via chemical reaction of a compound of formula II in free form or in protected and/or activated form; as well as, more specifically:

(E) A peptide in free or protected form, said peptide comprising a [1S,2R,3R]- or [1R,2S,3S]-1-nitrilo-1-carbonyl-3-methyl-2-oxy-heptane or -hept-5-ene residue and containing at least one synthetically formed peptide linkage, e.g. satisfying a free valency of the 1-nitrilo function and/or the free valency of the 1-carbonyl function of said residue.

In yet a further aspect the present invention also provides:

(F) A linear peptide comprising a [1S,2R,3R]- or [1R,2S,3S]-1-nitrilo-1-carbonyl-3-methyl-2-oxyheptane or -hept-5-ene residue, said peptide being in free or protected and in substantially pure form;

(G) A [1S,2R,3R]- or [1R,2S,3S]-1-nitrilo-1-carboxy-3-methyl-2-oxy-heptane or -hept-5-ene in free or in N-protected form and wherein a free valency of the 1-nitrilo function is satisfied by a peptide linkage; as well as (H) A [1S,2R,3R]- or [1R,2S,3S]-1-amino- or 1-methylamino-1-carbonyl-3-methyl-2-oxy-heptane or -hept-5-ene in free or N-protected form and wherein the free valency of the 1-carbonyl function is satisfied by a peptide linkage.

It will be understood that definitions (G) and (H) above relate specifically to peptides, e.g. peptides in accordance with definition (F), wherein the heptane or hept-5-ene moiety is at the C- and N-terminal of the peptide sequence respectively.

In the compounds defined under (D) through (H) above the 2-oxy radical may be e.g. 2-hydroxy. In the compounds defined under (D) through (G) above the 1-nitrilo radical may be a 1-imino or 1-methylimino radical. The compounds defined under (D), (E), (G) and (H) may be linear. They may if desired be isolated in pure or substantially pure form, e.g. in a form substantially free from other peptide contaminants. [The term "linear peptide" as used herein and in the accompanying claims denotes peptides having an N-and a C-terminal, which are not linked together, i.e. which do not complete a cyclic system. The term thus excludes peptides wherein the basic amino acid sequence is cyclic. It includes peptides comprising a minor, internal cyclic system, i.e. within the length of the amino acid sequence and completed by a non-peptide linkage. Preferably such "linear peptides" are acyclic. Both linear and acyclic peptides may of course bear one or more cyclic substituent groups along the length of the basic peptide chain.]

It will be appreciated that many of the compounds hereinabove described may exist in salt form. For example the free amino acids of formula II occur in non-salt form as well as acid salt, e.g. alkali-metal salt, and acid addition salt, e.g. hydrochloride salt form. Similarly peptides in accordance with the invention may occur in salt form in heavy metal complex form. Such forms are well-known in the art and may be obtained in conventional manner, e.g. from the non-salt form by reaction with an appropriate base, e.g. an alkali-metal hydroxide, or acid, e.g. hydrochloric acid (i.e. in the case of the free amino acids of formula II, by adjustment to a pH above or below the iso-electric point). In general such forms will be equivalent to the corresponding non-salt or non-complex forms. Accordingly, throughout the present specification and claims, compounds as defined are to be construed as embracing both non-salt and non-complex as well as, where appropriate, salt and/or complex forms.

The intermediates of formula XV through IV of flow-chart ② are also new and likewise form part of the present invention. Of these compounds, those of formula VIa and VIb through IV are of especial interest.

The following examples are illustrative of the methods of the present invention:

EXAMPLE 1

Synthesis of cyclosporin A

The synthetic sequence of the following example is that shown in the accompanying flow-chart ①. The following abbreviations are employed:

| BOC | = | t.Butyloxy-carbonyl. |
|---|---|---|
| Bzl | = | Benzyloxy. |
| H—α-Abu—OH | = | α-Aminobutyric acid. |
| H—Sar—OH | = | Sarcosine. |
| H—C$_9$A—OH | = | (2S,3R,4R,6E)-3-hydroxy-4-methyl-2-methylamino-oct-6-enoic acid (c.f. example 2.1). |
| Oxaz—C$_9$A—OH | = | (4R,5S)-4-(hex-2E-en-5R-yl)-1,2-trimethyl-oxazolin-5-carboxylic acid (c.f. example 7). |

In accordance with standard nomenclature all amino acid residues (e.g. -Abu-, -Leu-, -Ala-, -Val- etc..) are in the L-form unless otherwise indicated. Residues preceded by "Me" (e.g. as in "-MeLeu-") represent the corresponding N-methyl-residue.

Synthesis of protected Open-Chain form (a) Boc-α-Abu-Sar-Bzl:

10.3 ml (10.18 g=84.8 mMol) pivaloyl chloride and 16.4 g (162 mMol) N-methyl-morpholine are added to a solution of 15.66 g (17.1 mMol) Boc-α-Abu-OH in 500 ml chloroform and the mixture is stirred for 3 hrs. at room temperature under a nitrogen atmosphere. A solution of 16.5 g (92.5 mMol) H-Sar-Bzl in 500 ml chloroform are then added and the reaction mixture stirred for a further 2 hrs. at room temperature, again under a nitrogen atmosphere. The obtained solution is washed with 300 ml 1-N HCl, the aqueous phase extracted with 200 ml methylene chloride and the combined organic phases washed 2× with 200 ml saturated potassium carbonate solution. The aqueous phases are extracted with 200 ml methylene chloride and the combined organic phases dried over potassium carbonate, filtered and concentrated. The residue is chromatographed on 1 kg silica gel 60 (0.063–0.24 mm) using 1% methanol in methylene chloride as eluant, to yield the title compound: rotation, $[\alpha]_D^{25} = -42°$ (c=1.0 in chloroform).

(b) BOC-α-Abu-Sar-OH:

10.7 g (29.4 mMol) Boc-α-Abu-Sar-Bzl in 500 ml ethanol containing 2 g 10% palladium/charcoal are debenzylated by hydrogenation for 2 hrs. at room temperature. The product is filtered through talc, evaporated and dried to yield the title compound: Rotation, $[\alpha]_D^{25} = -5,3°$ (c=1.0 in chloroform).

(c) BOC-MeLeu-Ala-Bzl 23.3 ml (18.9 g=157 mMol) pivaloyl chloride and 48 ml (28.9 g=286 mMol) triethylamine are added to a solution of 35 g (143 mMol) BOC-MeLeu-OH in 500 ml chloroform and the mixture stirred for 2 hrs. at room temperature under a nitrogen atmosphere. 30.7 g (171 mMol) H-Ala-Bzl dissolved in 300 ml chloroform are then added and the reaction mixture stirred for a further 2 hrs. at room temperature, again under a nitrogen atmosphere. The product is purified in accordance with the technique of example 1a) to yield the title compound:

rotation, $[\alpha]_D^{25} = -59.4°$ (c=1.0 in chloroform).

(d) H-MeLeu-Ala-Bzl:

46.8 g (115 mMol) BOC-MeLeu-Ala-Bzl are dissolved in 100 ml trifluoroacetic acid pre-cooled to 0° C.

and allowed to stand for 1 hr. at 0° C. and ½ hr. at room temperature. The obtained solution is concentrated under vacuum, diluted with 500 ml methylene chloride, poured onto ice and washed with 300 ml saturated potassium carbonate solution. The aqueous phase is extracted with 200 ml methylene chloride, the combined organic phases dried over potassium carbonate, filtered and concentrated. The residue is chromatographed on 2 kg silica gel 60 (0.063–0,24 mm) using 5% methanol in methylene chloride as eluant to yield the title compound: rotation, $[\alpha]_D^{25} = -44.5°$ (c=1.0 in chloroform).

(e) BOC-Val-MeLeu-Ala-Bzl:

12.9 ml (12.7 g=106 mMol) pivaloyl chloride and 23 g (212 mMol) N-ethyl-diisopropylamine are added to a solution of 23.2 g (106 mMol) BOC-L-Val-OH in 400 ml chloroform and the mixture stirred for 2 hrs. at room temperature under a nitrogen atmosphere. 27.37 g (89 mMol) H-MeLeu-Ala-Bzl dissolved in 100 ml chloroform are then added and the reaction mixture stirred for a further 18 hrs. at 60° C. again under a nitrogen atmosphere. The obtained solution is washed with 300 ml 1 N HCl, the aqueous phase extracted with 200 ml methylene chloride and the combined organic phases washed 2× with 200 ml saturated potassium carbonate solution. The aqueous phases are extracted wit 200 ml methylene chloride, the combined organic phases dried over potassium carbonate, filtered and concentrated. The residue is chromatographed on 2 kg silica gel 60 (0.065–0.2 mm) with 1% methanol in methylene chloride as eluant to yield the title compound as a colourless oil: rotation $[\alpha]_D^{25} = -97.2$ (c=1.0 in chloroform).

(f) H-Val-MeLeu-Ala-Bzl:

30.7 g (60.8 mMol) BOC-Val-MeLeu-Ala-Bzl dissolved in 100 ml trifluoroacetic acid are stirred for 2 hrs. at room temperature. The obtained solution is concentrated under vacuum and the residue diluted with 500 ml methylene chloride. The solution is washed 3× with 200 ml saturated potassium carbonate solution, ice being added, the aqueous phases extracted with 200 ml methylene chloride and the combined organic phases dried over potassium carbonate. The title compound is obtained as a pale-yellow oil after further filtration and concentration: rotation, $[\alpha]_D^{25} = -87.1°$ (c=1.0 in chloroform).

(g) BOC-MeLeu-Val-MeLeu-Ala-Bzl:

8.5 ml (8.3 g=69.5 mMol) pivaloyl chloride and 12.7 ml (115.8 mMol) N-methylmorpholine are added to a solution of 15.6 g (63.7 mMol) BOC-MeLeu-OH in 500 ml chloroform and the mixture stirred for 2 hrs. at room temperature under a nitrogen atmosphere. 23.45 g (57.9 mMol) H-Val-MeLeu-Ala-Bzl dissolved in 100 ml chloroform are then added and the reaction mixture stirred for a further 2 hrs. at room temperature again under a nitrogen atmosphere. After purification in accordance with the procedure of example 1a the title compound is obtained as a pale yellow oil: rotation, $[\alpha]_D^{25} = -126.7°$ (c=1.0 in chloroform).

(h) H-MeLeu-Val-MeLeu-Ala-Bzl:

31.27 g (49.5 mMol) BOC-MeLeu-Val-MeLeu-Ala-Bzl dissolved in 100 ml trifluoroacetic acid are stirred for 2½ hrs. at room temperature and the product solution concentrated under vacuum. The residue is diluted with 500 ml methylene carbonate solution, ice being added and the aqueous phases extracted with 200 ml methylene chloride. The combined organic phases are dried over potassium carbonate, filtered and concentrated to yield the title compound: rotation $[\alpha]_D^{22} = -114.4°$ (c=1.0 in chloroform), M.P. on recrystallisation from ether/petrol ether=66°–67°

(i) BOC-α-Abu-Sar-MeLeu-Val-MeLeu-Ala-Bzl:

3.5 ml (3.3 g=27.7 mMol) pivaloyl chloride and 5.4 g (52.9 mMol) N-methylmorpholine are added to a solution of 6.9 g (25.2 mMol) BOC-α-Abu-Sar-OH (example 1b) in 250 ml chloroform and the mixture stirred for 1 hr. at room temperature under a nitrogen atmosphere. 12.0 g (22.7 mMol) H-MeLeu-Val-MeLeu-Ala-Bzl dissolved in 100 ml chloroform are then added and the reaction mixture stirred for a further 15 hrs. at room temperature, again under a nitrogen atmosphere. The obtained product is purified in accordance with the procedure of example 1a to yield the title compound as a colourless foam: rotation, $[\alpha]_D^{25} = -137.9°$ (c=1.0 in chloroform).

(j) H-α-Abu-Sar-MeLeu-Val-MeLeu-Ala-Bzl:

15.75 g (19.9 mMol) BOC-α-Abu-Sar-MeLeu-Val-MeLeu-Ala-Bzl dissolved in 50 ml trifluoroacetic acid are stirred for 4 hrs. at room temperature. The solvent is evaporated under vacuum, the residue dissolved in 300 ml methylene chloride and the obtained solution washed 3× with 200 ml saturated sodium carbonate solution, ice being added. The Aqueous phases are extracted with 200 ml methylene chloride, and the combined organic phases dried over potassium carbonate, filtered and concentrated to yield the title compound: rotation, $[\alpha]_D^{25} = -127.3°$ (c=1.0 in chloroform).

(k) Oxaz-C$_9$A-α-Abu-Sar-MeLeu-Val-MeLeu-Ala-Bzl:

1.5 g (6.22 mMol) freshly prepared Oxaz-C$_9$A-OH are dissolved in 50 ml tetrahydrofuran, and 0.7 g (6.93 mMol) N-methyl-morpholine are immediately added. 1.68 g (12.4 mMol) 1-hydroxybenzotriazole are dehydrated by shaking and concentrating 2× with 50 ml toluene and are then added to the solution together with 4.28 g (6.22 mMol) H-α-Abu-Sar-MeLeu-Val-MeLeu-Ala-Bzl.

The whole is cooled to 0° C. and 1.34 g (6.5 mMol) dicyclohexylcarbodiimide are added. The obtained reaction mixture is allowed to warm to room-temperature and is then stirred for 15 hrs. at room-temperature. The obtained solution is diluted with 300 ml methylene chloride and shaken with 200 ml 1 N sodium bicarbonate solution. The aqueous phase is re-extracted with 200 ml methylene chloride, and the combined organic phases are dried over sodium sulfate, filtered and evaporated. The residue is chromatographed on 500 g silica gel (0.063–0.24 mm) using 3% methanol in methylene chloride as eluant, to yield the title compound: rotation $[\alpha]_D^{25} = -117°$ (c=1.0 in chloroform).

(l) H-C$_9$A-Abu-Sar-MeLeu-Val-MeLeu-Ala-Bzl:

1.5 g (1.6 mMol) Oxaz-C$_9$A-α-Abu-Sar-MeLeu-Val-MeLeu-Ala-Bzl dissolved in 16 ml methanol are stirred for 15 hrs. at room temperature in the presence of 1.6 ml 1 N HCl. The splitting off of the isopropylidene protecting group may be followed by means of thin-layer chromatography. The acid in the reaction medium is neutralised by the addition of 1 g (12 mMol) sodium bicarbonate and the methanol carefully and fully evaporated off, the temperature being kept at a maximum of 30° C. The residue is taken up in 10 ml methylene chloride containing 5% methanol and chromatographed on 100 g silica gel (0.06–0.24 mm) using 5% methanol in methylene chloride as eluant. The title compound is obtained with a rotation of $-138°$ (c=1.0 in chloroform).

(m) BOC-(D)-Ala-MeLeu-Bzl:

18.9 g (100 m mol) Boc-(D)-Ala-OH are dissolved in 250 ml chloroform and cooled with stirring to −20° C. 23.1 ml (21.2 g=210 m mol) N-methylmorpholine and 12.2 ml (12.0 g=100 m mol) pivaloyl chloride are then added and the whole stirred for 2 hours, still at −20° C. Anhydride formation is followed by means of IR control. When anhydride formation is complete 23.5 g (100 m mol) H-MeLeu-Bzl dissolved in 50 ml chloroform are added dropwise to the obtained reaction mixture at −20° C. and over a period of 5 minutes. Formation of the dipeptide is followed using thin-layer chromatography and IR-spectrometry. After 19 hours no further anhydride can be detected. The obtained reaction solution is poured onto 300 ml water and diluted with 300 ml chloroform. The organic phase is separated, washed with 100 ml water, dried over sodium sulphate, filtered and the solvent carefully evaporated off at max. 40° C. The obtained residue is recrystallised from hexane to yield the title compound: rotation $[\alpha]_D^{25} = -35.3°$ C. (c=1,05 m chloroform; M.P.=81° C.

(n) BOC-(D)-Ala-MeLeu-OH:

32.45 g (79.92 m mol) BOC-(D)-Ala-MeLeu-Bzl in 800 ml ethanol containing 1.6 g 10% palladium/charcoal are debenzylated by hydrogenation for 2 hours at room temperature. After uptake of the calculated quantity of hydrogen the suspension is filtered through talc, the solvent evaporated off and the residue crystallised from hexane to yield the title compound with a rotation of $[\alpha]_D^{25} = -36.7°$ (c=0.8 in chloroform).

(o) BOC-(D)-Ala-MeLeu-MeLeu-Bzl:

17.9 ml (16.4 g=162.4 m mol) N-methylmorpholine are added to a solution of 24.5 g (77.3 m mol) BOC-(D)-Ala-MeLeu-OH dissolved in 200 ml chloroform and the whole is cooled to −20° C. 9.5 ml (9.27 g=77.3 m mol) pivaloyl chloride are then added over 5 minutes and the reaction mixture stirred for 90 minutes, still at −20° C. Anhydride formation is followed by means of IR control and when complete a solution of 18.2 g (77.3 m mol) H-MeLeu-Bzl in 50 ml chloroform is added dropwise at −20° within 5 minutes. A reaction period of 18 hours at −20° C. is required until no more anhydride is present. The obtained solution is poured onto 300 ml water and is extracted in a separating funnel after first diluting with a further 300 ml chloroform. The aqueous phase is extracted with 300 ml chloroform, the combined organic phases dried over sodium sulphate, filtered and evaporated. The residue is chromatographed on 1 kg silica gel (0.063–0.24 mm) using 2% methanol in methylene chloride as eluant to yield the title compound: rotation, $[\alpha]_D^{25} = -101.3°$ (c=0.9 in chloroform).

(p) BOC-(D)-Ala-MeLeu-MeLeu-OH:

29.3 g (54.97 m mol) BOC-(D)-Ala-MeLeu-MeLeu-Bzl in 800 ml ethanol containing 1.5 g 10% palladium/charcoal are debenzylated by hydrogenation for 2 hours at room temperature. After uptake of the calculated amount of hydrogen, the obtained suspension is filtered through talc, evaporated and the residue crystallised from hexane to yield the title compound: rotation $[\alpha]_D^{25} = -112.6°$ (c=0.85 in chloroform).

(q) BOC-(D)-Ala-MeLeu-MeLeu-MeVal-Bzl:

3.48 ml (3.18 g=31.5 m mol) N-methylmorpholine and 1.86 ml (1.8 g=15.0 m mol) pivaloyl chloride are added to a solution of 6.65 g (1.50 m mol) BOC-(D)-Ala-MeLeu-MeLeu-OH in 60 ml chloroform, pre-cooled to −20° C. Conversion to the anhydride is completed after stirring for 2 hours at −20° C. (IR control). 3.35 g (15.0 m mol) H-MeVal-Bzl in 50 ml chloroform are then added dropwise to the reaction mixture at −20° C. The progress of the reaction is followed by means of thin-layer chromatography and IR-spectrometry and is complete after 4½ days. The obtained solution is poured onto 200 ml 1 N sodium bicarbonate on a shaker, and diluted with 300 ml chloroform. After separation of the organic phase, the aqueous phase is extracted with a further 100 ml chloroform, the combined chloroform phases dried over sodium sulphate, filtered and evaporated. The residue is chromatographed on 600 g silica gel (0.063–0.2 mm) using 2% methanol in methylene chloride as eluant to yield the title compound: rotation, $[\alpha]_D^{25} = -143.7°$ (c=0.9 in chloroform).

(r) BOC-(D)-Ala-MeLeu-MeLeu-MeVal-OH:

5.53 g (10.0 m mol) of BOC-(D)-Ala-MeLeu-MeLeu-MeVal-Bzl dissolved in 500 ml ethanol containing 0.5 g 10% palladium/charcoal are debenzylated by hydrogenation for 1 hour at room-temperature. The obtained suspension is filtered through talc, evaporated and the residue dried over sodium sulphate to yield the title compound with a rotation of $[\alpha]_D^{25} = -187°$ (c=0.88 in chloroform).

(s) BOC-(D)-Ala-MeLeu-MeLeu-MeVal-C$_9$A-α-Abu-Sar-MeLeu-Val-MeLeu-Ala-Bzl:

278 ml (0.5 m mol) BOC-(D)-Ala-MeLeu-MeLeu-MeVal-OH followed by 479 mg (0.55 m mol) H-C$_9$A-α-Abu-Sar-MeLeu-Val-MeLeu-Ala-Bzl (c.f. example 1 l) are dissolved in 10 ml methylene chloride at room temperature. 0.55 ml (50.5 mg=0.5 m mol) N-methylmorpholine diluted with 1 ml methylene chloride and 22.1 mg (0.5 m mol) benzotriazolyl-N-oxy-tris-(dimethylamino)phosphonium hexafluorophosphate are then added to the solution and the whole is stirred for 22 hours at room temperature, the course of the reaction being followed to completion by means of thin-layer chromatography. The product solution is diluted with 200 ml methylene chloride, washed with 100 ml water and the aqueous phase extracted with 100 ml methylene chloride. The combined organic phases are dried over sodium sulphate, filtered and evaporated. The residue is chromatographed on 200 g silica gel (0.063–0.24 mm) using 5% methanol in methylene chloride as eluant to yield the title compound: rotation, $[\alpha]_D^{25} = -175.6$ (c=0.86 in chloroform).

Cyclisation Steps—Carbonylazide method (t) BOC-(D)-Ala-MeLeu-MeLeu-MeVal-C$_9$A-α-Abu-Sar-MeLeu-Val-MeLeu-Ala-NHNH$_2$:

0.84 g (0.59 m mol) BOC-(D)-Ala-MeLeu-MeLeu-MeVal-C$_9$A-α-Abu-Sar-MeLeu-Val-MeLeu-Ala-Bzl are stirred for 4 hours at room temperature with 3 ml hydrazine hydrate in 3 ml dimethylformamide, and the dimethylformamide and excess hydrazine hydrate are thereafter evaporated off at room temperature under high vacuum. The residue is dissolved in 250 ml ethylacetate and shaken 2 times with 50 ml saturated NaCl solution. The organic phase is dried over sodium sulphate, filtered and evaporated and the residue chromatographed on 100 g silica gel (0.663–0.24 mm) using 5% methanol in methylene chloride as eluant to yield the title compound: rotation $[\alpha]_D^{20} = -170.2°$ (c=1.0 in chloroform).

(u) H-(D)-Ala-MeLeu-MeLeu-MeVal-C$_9$-A-α-Abu-Sar-MeLeu-Val-MeLeu-Ala-NHNH$_2$:

0.73 g (0.55 m mol) BOC-(D)-Ala-MeLeu-MeLeu-MeVal-C$_9$A-α-Abu-Sar-MeLeu-Val-MeLeu-Ala-NHNH$_2$ are stirred for 1 hour at room temperature in 3 ml trifluoroacetic acid under anhydrous conditions, and the trifluoroacetic acid is subsequently fully evaporated off at room temperature under water-suction vacuum. The residue is dissolved in 200 ml methylene chloride and shaken immediately with 100 ml saturated sodium bicarbonate solution. The organic phase is dried over sodium sulphate, filtered and evaporated and the obtained residue chromatographed on 100 g silica gel using 10% methanol in methylene chloride as eluant, to yield the title compound: rotation $[\alpha]_D^{20} = -189.2$ (c=0.87 in chloroform).

(v) Cyclosporin A:

0.2 ml 2 M HCl/dioxane and 22.8 mg (0.22 m mol) t-butylnitrite are added to 136 mg (0.11 m mol) H-(D)-Ala-MeLeu-MeLeu-MeVal-C9-A-α-Abu-Sar-MeLeu-Val-MeLeu-Ala-NHNH$_2$ dissolved in 5 ml dimethylformamide at a temperature of $-20°$ C. and the whole is stirred for 45 minutes at $-20°$ C. A further 22.8 mg (0.22 m mol) t-butylnitrite are then added and the reaction mixture stirred for a further 2 hours at $-20°$ C., before being diluted with 20 ml dimethyl formamide. 0.051 g (0.4 m mol) ethyldiisopropylamine are then added and the mixture stirred for a further 2 hours at $-20°$ C. The product solution is poured onto 100 ml HCl at pH 3 and shaken with 200 ml diethyl ether. The ether phases are washed with 50 ml water, dried over sodium sulphate, filtered and evaporated, the residue is chromatographed on 50 g silica gel (0.063–0.24 mm) using 2% methanol in methylene chloride as eluant. Fractions identified as Cyclosporin A by thin layer chromatography are collected and recrystallised from acetone. The obtained product has a melting point of 150° C. and a rotation of $[\alpha]_D^{20} = -245°$ (c=0.8 in chloroform). Identity with the naturally occurring compound Cyclosporin A is confirmed by NMR spectroscopy.

Cyclisation Steps-Castro-Ester Method.

(w) Boc-(D)-Ala-MeLeu-MeLeu-MeVal-C9A-α-Abu-Sar-MeLeu-Val-MeLeu-Ala-OH:

7.1 ml of 0.2 N aqueous NaOH are added to a solution of 2.0 g (1.42 mMol) Boc-(D)-Ala-MeLeu-MeLeu-MeVal-C9A-α-Abu-Sar-MeLeu-Val-MeLeu-Ala-Bzl [see Example (1 s)] in 50 ml ethanol and the reaction mixture allowed to stand for 24 hours at 0° C. The obtained clear, colourless solution is adjusted to pH 5 by the addition of a few drops of concentrated acetic acid and fully evaporated at 40° C. under vacuum. The remaining amorphous residue is shaken with 100 ml water and 2× with 200 ml methylene chloride, and the organic phase dried over Na$_2$SO$_4$, filtered and evaporated to yield a white foam. This is then chromatographed on 400 g silica gel 60 and collected in 30 ml fractions using methylene chloride, together with an additional 10% methanol as eluant. From fraction 80 onwards, 30% methanol is used as eluant. The title compound is recovered from fractions 81 onwards by thin-layer chromatography on silica-gel using CH$_2$Cl$_2$/30% MeOH as eluant: rotation $[\alpha]_D^{20} = -173°$ C. (c=1 in chloroform).

(x) H-(D)-Ala-MeLeu-MeLeu-MeVal-C9A-α-Abu-Sar-MeLeu-Val-MeLeu-Ala-OH:

A 100 ml double-necked flask provided with a stirrer and CaCl-tube and containing 1.2 g (0.91 mMol) BOC-(D)-Ala-MeLeu-MeLeu-MeVal-C9A-α-Abu-Sar-MeLeu-Val-MeLeu-Ala-OH is cooled in an ice-bath at $-20°$ C. and 20 ml trifluoroacetic acid pre-cooled to $-20°$ C. are added with stirring. The obtained clear and virtually colourless solution is stirred for a further 1 hour at $-20°$ C., and the trifluoroacetic acid evaporated off, still at $-20°$ C., using a water-pump-vacuum. The remaining oil is diluted with 200 ml methylene chloride and shaken in a separating funnel with 100 ml saturated NaHCO$_3$ solution. The organic phase is dried over Na$_2$SO$_4$, filtered and the solvent fully evaporated. The obtained white foam is rubbed with 25 ml other and filtered through a glass frit. The title compound is obtained after chromatography on silica gel using CH$_2$Cl$_2$/20% MeOH as eluant as a white powder: rotation $[\alpha]_D^{20} = -201.8°$ C. (c=1 in chloroform).

(y) Cyclosporin A:

0.08 ml N-methyl-morpholine and 326 mg (0.738 mMol) benzotriazol-1-yl-oxy-tris-(dimethylamino)-phosphonium-hexafluorophosphate [Castro-reagent] are added to a solution of 900 mg (0.738 mMol) H-(D)-Ala-MeLeu-MeLeu-MeVal-C9A-α-Abu-Sar-MeLeu-Val-MeLeu-Ala-OH in 60 ml methylene chloride in a double-necked flask and the reaction mixture stirred for 3 days at 20° C. The obtained solution is diluted with 200 ml methylene chloride and shaken with 50 ml water. The organic phase is dried over Na$_2$SO$_4$, filtered and evaporated. The amorphous residue is then chromatographed on 200 g silica gel 60 using methylene chloride with 4% MeOH as eluant. The eluate is collected in 30 ml fractions. Cyclosporin A is recovered from fractions 28 through 39 and purified by crystallisation from acetone/ether and re-crystallisation from acetone: rotation $[\alpha]_D^{20} = -243.6°$ C. (c=1 in chloroform). Identity with the naturally occurring compound Cyclosporin A is confirmed by NMR spectroscopy and by x-ray powder diagram according to the method of Guiner and Devolls.

EXAMPLE 2.1

Synthesis of (2S,3R,4R,6E)-3-hydroxy-4-methyl-2-methylamino-oct-6-enoic acid: flow-chart (2), formula II [R$_1$=CH$_3$, -x-y-=trans-CH=CH-], process step s 172 mg (0.76 mMol) (4R,5S)-4-(hex-2E-en-5R-yl)-1-methyl-2-oxo-oxazolin-5-carboxylic acid (product of example 2r) are dissolved in 2.0 ml 2 N KOH. The solution is warmed for 3 hrs. at 80° C., cooled, adjusted to pH 5 by the addition of 1 N HCl and concentrated on a rotary evaporator. The residue is taken up in methanol, filtered through 50 g Sephadex LH 20 and evaporated. The residue is re-crystallised from ethanol to yield the title compound in pure form: M.p. 240°–241° C.; rotation, $[\alpha]_D^{22} = +13.0°$ (c=0.46 in water).

EXAMPLE 2.2

Synthesis of (2S,3R,4R)-3-hydroxy-4-methyl-2-methylamino-octanoic acid: flow-chart (2), formula II [R$_1$=CH$_3$, -x-y-=-CH$_2$-CH$_2$-], process step s 110 mg (0.48 mMol) (4R,5S)-4-(2R-hexyl)-1-methyl-2-oxo-oxazolin-5-carboxylic acid (product of example 2r') are dissolved in 1.4 ml 2 N KOH. The solution is warmed for 2 hrs. at 80° C., cooled, adjusted to pH 4 by the addition of 1 N HCl and filtered through 50 g Sephadex LH 20 using methanol as solvent. The filtrate is evaporated, the residue taken up in 25 ml water, freed from contaminating HCl by passing through 3 g of an anion-exchange resin [Biorad AG 3-×4 (100–200 mesh)], evaporated and re-crystallised from ethanol to yield the title compound in pure form: M.p. 248°–249°; rotation, $[\alpha]_D^{22} = +17.0°$ (c=0.44 in water).

The starting materials for use in the foregoing examples 2.1 and 2.2 are produced as follows:

EXAMPLES 2a (4S,5S)-4,5-dibenzyloxymethyl-2-phenyl-1,3-dioxolan: flow-chart ②, formula XVII [X' and X"=φ-CH$_2$-]

15 g (71.4 mMol) (4S,5S)-4,5-dihydroxymethyl-2-phenyl-1,3-dioxolan are rendered completely anhydrous by evaporating 2× with 300 ml toluene and the oil remaining in the reaction vessel is dissolved in 150 ml toluene, 30 g powdered KOH (535 mMol) and 71.5 g (418 mMol) benzyl bromide are added and the reaction mixture stirred for 15 hours at 80° C. The mixture is cooled, the remaining toluene-phase decanted, and the inorganic component removed from the residual phase by stirring 2× with 200 ml toluene and decanting. The combined toluene phases are filtered through talc, evaporated and the remaining oil filtered fraction-wise through 2 kg silica gel 60 using methylene chloride as solvent. Fractions containing benzyl bromide are disposed of. The title compound is obtained as a light yellow fluid with a rotation of $[\alpha]_D^{20} = +10.1 \ (\pm 1)°$ (c=1.4 in chloroform).

EXAMPLE 2b (2S,3R)-2-benzoyloxy-1,4-dibenzyloxy-3-bromobutane: flow-chart ②, formula XVI [X' and X"=φ-CH$_2$-].

10.9 g (61.2 mMol) N-bromosuccinimide are suspended in 150 ml tetrachloromethane, the suspension cooled to 4° C. and 23.9 g (61.2 mMol) of (4S,5S)-4,5-dibenzyloxymethyl-2-phenyl-1,3-dioxolan dissolved in 250 ml tetrachloromethane added dropwise at the same temperature over a period of 50 minutes. The cooling bath is removed, the reaction flask wrapped in aluminium foil and the reaction mixture stirred for 3 days at room temperature. The obtained orange coloured suspension is diluted with 1 liter methylene chloride and shaken with 200 ml saturated sodium bicarbonate solution. The aqueous phase is extracted with 300 ml methylene chloride and the combined organic phases are dried over sodium sulfate, filtered through a layer of talc and evaporated under vacuum. The residue is chromatographed using 1 kg of silica gel 60 and methylene chloride as eluant. The title compound is obtained as a colourless oil: rotation, $[\alpha]_D^{22} = +18.7°$, (c=1.3 in chloroform).

EXAMPLE 2c (2S,3S)-dibenzyloxymethyl-oxiran: flow-chart ②, formula XV [X' and X"=φ-CH$_2$-]

16.5 ml aqueous 10 N potassium hydroxide are added to a solution of 25.7 g (54.8 mMol) of (2S,3R)-2-benzoyloxy-1,4-dibenzyloxy-3-bromo-butane in 330 ml ethanol, to give a substantially concommitant precipitation of KBr. The reaction mixture is stirred for 30 minutes at room temperature and then adjusted to pH 5 by the addition of 10 N HCl. The aqueous-ethanolic mixture is evaporated under vacuum, the residue taken up in 500 ml methylene chloride, washed with 200 ml water and the aqueous phase extracted 2× with 200 ml methylene chloride. The combined organic phases are dried over sodium sulfate, filtered through a layer of talc, evaporated and the residue distilled under vacuum to yield the title compound: B.P. 164°-168° C. at 0.2 Torr; rotation, $[\alpha]_D^{20} = -8.7°$ (c=1,1 in chloroform). The product crystalises in ether/petrolether: M.P. 24° C.

EXAMPLE 2d (2R,3R)-1,4-dibenzyloxy-2-hydroxy-3-methyl-butane: flow-chart ②, formula XIV [X' and X"=φ-CH$_2$-]

4.64 g (24.38 mMol) of vacuum dried cuprous iodide are suspended in 100 ml abs. diethylether with dry nitrogen gassing. 23.6 ml (47.52 mMol) of a 4.4% solution of methyllithium in ether are added rapidly at 0° C. and the obtained clear orange-brown solution cooled immediately to −60° using a dry-ice cooling bath. 3.0 g (10.56 mMol) of (2S,3S)-dibenzyloxymethyl-oxiran dissolved in 25 ml abs. ether are then added and the reaction mixture stirred for 1 hour still at −60° C. 5 ml methanol are then added in order to destroy excess methyllithium. The cooling bath is then removed, the reaction mixture warmed to room temperature and 5 ml of water added. The reaction mixture is diluted with 300 ml methylene chloride washed 3× with 200 ml water and the aqueous copper coloured precipitates extracted a further 3× with 200 ml methylene chloride. The combined organic phases are dried over sodium sulfate, filtered through a layer of talc, evaporated under vacuum and the residue purified by chromatographing on 90 g silica gel 60 using methylene chloride as eluant to yield the title compound as a light-beige oil: rotation, $[\alpha]_D^{20} = -4,4°$ (c=1.5 in chloroform).

EXAMPLE 2e (2R,3R)-1,2,4-trihydroxy-3-methyl-butane: flow-chart ②, formula XIII 4.5 g (15 mMol) (2R,3R)-1,4-dibenzyloxy-2-hydroxy-3-methyl-butane are de-benzylated by hydrogenation in 120 ml ethanol containing 0.5 g of 10% palladium/charcoal for 2 hours at room-temperature. The product is filtered through talc, evaporated and chromatographed on 120 g silica gel 60, with methylene chloride/methanol (8:2) as eluant. The title compound is obtained as a colourless, viscous oil.

EXAMPLE 2f (4R)-4-(1-hydroxy-2R-propyl)-2-dimethyl-1,3-dioxolan: flow-chart ②, formula XII 30.5 g (0.254 Mol) (2R,3R)-1,2,4-trihydroxy-3-methyl-butane dissolved in 180 ml benzene are refluxed for 2 hours with 39.8 g (0.381 Mol) 2,2-dimethoxypropane and 180 mg p-toluenesulfonic acid mono-hydrate. The solvent is removed on a rotary evaporator, the remaining oil taken up in 600 ml acetone, 0.6 g p-toluenefulfonic acid mono-hydrate are added and the obtained solution boiled for 16 hours under reflux. The obtained yellow solution is concentrated to 100 ml on a rotary evaporator and chromatographed on 1 kg neutral Alox (activity: II) using 2% methanolic methylene chloride as eluant. The title compound is obtained as an oil: rotation, $[\alpha]_D^{22} = -19.8°$ (c=1.0 in chloroform; B.P.=56° C. at 0.1 Torr.

EXAMPLE 2g (4R)-4-(1-p-tosyloxy-2R-propyl)-2-dimethyl-1,3-dioxolan: flow-chart ②, formula XI.

14.3 g (75 mMol) p-toluenesulfonyl-chloride are added at room temperature to a solution of 10.0 g (62.5 mMol) of (4R)-4-(1-hydroxy-2R-propyl)-2-dimethyl-1,3-dioxolan in 65 ml chloroform. 10.1 ml absolute pyridine are added, whereupon the temperature rises to 31° C. The exothermic reaction continues for a further 45 minutes before the temperature begins to sink. The reaction mixture is thereupon stirred for a further 3 hours at 35° C. to complete reaction. The obtained solution is diluted with 300 ml methylene chloride, washed 1× with 150 ml saturated sodium carbonate and 2× with 150 ml saturated cuprous sulfate. The aqueous phases are extracted with 200 ml methylene chloride, the combined organic phases dried over sodium sulfate, filtered through talc and evaporated. The residue is chromatographed on 400 g neutral Alox (activity: II) using methylene chloride as eluant. After crystallisation from petrol ether, the title compound is obtained with a rotation $[\alpha]_D^{20} = +14.2$ (c = 1.0 in chloroform); M.p. = 39°–40° C.

EXAMPLE 2h (4R)-4-(1-cyano-2R-propyl)-2-dimethyl-1,3-dioxolan: flow-chart ②: formula X The crystalline (4R)-4-(1-p-tosyloxy-2R-propyl)-2-dimethyl-1,3-dioxolan (17.0 g = 54.1 mMol) obtained in accordance with example 2g is hygroscopic. The crystals are accordingly dissolved immediately in 90 ml dimethylsulfoxide, 4.38 g (70.4 mMol) KCN are added and the obtained reaction mixture stirred for 3 days at room temperature under nitrogen. The obtained solution is diluted with 250 ml toluene, shaken with 125 ml water, the aqueous phase extracted 2× with 300 ml methylene chloride, evaporated and the residue taken up in 100 ml water. After shaking 2× with 200 ml toluene the organic phases are combined with the first toluene phase, dried over sodium sulphate, filtered, concentrated and distilled under high vacuum to yield the title compound as a colourless oil: B.P. = 60°–63° C. at 0.03 Torr; rotation $[\alpha]_D^{22} = +11.2$ (c = 1.0 in chloroform).

EXAMPLE 2i (3R)-3-(4R-2-dimethyl-1,3-dioxolanyl)butyraldehyde: flow-chart ②: formula IX 41 g (243 mMol) of (4R)-4-(1-cyano-2R-propyl)-2-dimethyl-1,3-dioxolan are dissolved in 1 liter hexane and the solution cooled to −78° C. 205 ml diisobutylaluminium hydride (in the form of a 20% solution in hexane) are added drop-wise under a nitrogen atmosphere over 30 minutes in such a way that the temperature does not rise over −70° C. The reaction mixture is thereafter stirred for a further 1½ hours at −78° C. Excess reducing agent is then decomposed by the addition of 15 ml water in 60 ml tetrahydrofuran at −70° C. under a nitrogen atmosphere. The obtained reaction mixture is poured onto 1 liter water and shaken. The precipitated Lithiumaluminium sediment is removed with a suction filter. The filtrate is separated from the aqueous phase in a separating funnel and shaken 2× with 300 ml methylene chloride. The combined organic phases are dried over sodium sulfate, filtered, concentrated on a rotary evaporator under reduced pressure and chromatographed on 3 kg silica gel 60 using 2% methanolic methylene chloride as eluant. The title compound is obtained after high-vacuum distillation under a nitrogen atmosphere as a colourless oil: B.P. 45°–50° C. at 0.03 Torr.

EXAMPLE 2j (4R)-4-(hex-2E-en-5R-yl)-2-dimethyl-1,3-dioxolan: flow-chart ②, formula VIII 19.0 g (51.1 mMol) of ethyltriphenylphosphonium bromide are dried over-night under high-vacuum at 110° C. and made up in solution in 250 ml tetrahydrofuran and 250 ml ether under a nitrogen atmosphere. 1.1 molar equivalents of n-butyl-lithium (31.2 ml of a 15% solution in hexane) are then added with nitrogen gassing within 20 minutes in such a way that the temperature does not rise above 30° C. The reaction mixture takes on a strong red colouration and is stirred for a further 30 minutes at room temperature before colling to −78° C. 8.0 g (46.5 mMol) (3R)-3-(4R-2-dimethyl-1,3-dioxolanyl)-butyraldehyde dissolved in 50 ml absolute diethylether are then added drop-wise so that the temperature does not rise above −73° C. The reaction mixture is then stirred for a further 30 minutes and takes on a light-yellow colouration. A further 31.2 ml (51.1 mMol) n-butyl-lithium dissolved in hexane are then added at −78° C. and the reaction mixture again stirred for 30 minutes. The reaction mixture is warmed to −30° C. and 6.5 ml (69.7 mMol) t.-butanol added drop-wise within 10 minutes. The reaction mixture is stirred for a further 10 minutes at −30° C. and 7.8 g (69.7 mMol) potassium t.-butylate are then added in one go. The reaction solution, which is now yellow, is warmed to room temperature, stirred for 1½ hours and poured onto 1 liter water. The aqueous phase is removed in a separating funnel and shaken 4× with 200 ml ether. The combined organic phases are dried over sodium sulfate, filtered off and concentrated on a rotary evaporator under reduced pressure to yield the title compound. This is used directly for further reaction without intermediate purification.

EXAMPLE 2k (2R,3R,5E)-2-hydroxy-3-methyl-5-hepten-1-ol: flow-chart ②, formula VIIa [Z = trans $CH_3\text{-}CH\text{=}CH\text{-}CH_2\text{-}$]

40 ml water and 40 ml 1 N HCl are added to a solution of 6.5 g (35 mMol) (4R)-4-(hex-2E-en-5R-yl)-2-dimethyl-1,3-dioxalan in 300 ml tetrahydrofuran and the reaction mixture allowed to stand for 2 days at room-temperature. The reaction mixture is then adjusted to pH 6–7 by the addition of saturated sodium bicarbonate, the tetrahydrofuran evaporated off in a rotary evaporator and the aqueous solution extracted with methylene chloride until it reacts negatively when tested for the presence of diols. The combined organic phases are dried over sodium sulfate, filtered, concentrated on a rotary evaporator and filtered through 500 g silica gel 60 using 10% methanolic methylene chloride as eluant, to yield the title compound as a colourless oil: rotation, $[\alpha]_D^{22} = -5.7°$ (c = 1.0 in chloroform), and exhibiting the strong IR-absorption at 970 cm$^{-1}$ characteristic for a trans-double bond.

EXAMPLE 2l (2R,3R,5E)-2-[(1-ethoxyethyl)-1]oxy-3-methyl-5-hepten-1-ol: flow-chart ②, formula VIIb [Z = trans $CH_3\text{-}CH\text{=}CH\text{-}CH_2\text{-}$; $X_3 = C_2H_5O\text{-}CH(CH_3)\text{-}$]

6.81 ml (58.62 mMol) benzoyl chloride are added over a period of 10 minutes to a solution of 9.0 g (55.8 mMol) of (2R,3R,5E)-2-hydroxy-3-methyl-5-hepten-1-ol in 90 ml pyridine, pre-cooled to 0° C. The reaction mixture is stirred for 40 minutes at room temperature, diluted with 600 ml methylene chloride and washed 3× with 200 ml cuprous sulfate. The aqueous phases are extracted with 200 ml methylene chloride, the organic phases combined, dried over sodium sulfate, filtered, evaporated and chromatographed on 500 g silica gel 60 using 1% methanolic methylene chloride as eluant. The obtained (2R,3R,5E)-1-benzyloxy-2-hydroxy-3-methyl-5-heptene is dissolved in 200 ml methylene chloride. 14.4 g ethylvinylether and a catalytic amount of trifluoroacetic acid are added and the reaction mixture stirred for 3 days at room temperature. The obtained solution is chromatographed on 800 g basic Alox (activity II) using 1% methanolic methylene chloride as eluant, and the obtained (2R,3R,5E)-2-[(1-ethoxyethyl)-1]oxy-1-benzoyloxy-3-methyl-5-heptene dissolved in 150 ml ethanol. 30 ml 10 N potassium hydroxide solution are then added and the reaction mixture stirred for 90 minutes at room temperature. The obtained solution is diluted with 1 liter methylene chloride, washed with 400 ml water and the aqueous phase extracted with 400 ml methylene chloride. The combined organic phases are dried over sodium sulfate, filtered and evaporated to yield the title compound as a colourless oil, which is used without purification for further reaction.

Example 2m'

(2R,3R,5E)-2-[(1-ethoxyethyl)-1]oxy-3-methyl-5-hepten-1-aldehyde: flow-chart ②, formula VIb [Z=trans $CH_3-CH=CH-CH_2-$; $X_3=C_2H_5O-CH(CH_3)-$].

6.3 g (21.3 mMol) of (2R,3R,5E)-2-[(1-ethoxyethyl)-1]oxy-3-methyl-5-hepten-1-ol dissolved in 120 ml dimethylsulfoxide/benzene (1:1) are stirred for 2 hours at room temperature with 0.8 ml (10.65 mMol) trifluoroacetic acid and 18.5 g (89.67 mMol) dicyclohexylcarbodiimide. The obtained suspension is filtered with a suction filter, the filtrate taken up in 500 ml ether and washed with 250 ml water. The aqueous phase is extracted with 300 ml ether, the organic phase dried over sodium sulfate, filtered and evaporated. The residue is chromatographed on silica gel 60 using 0.5% methanolic methylene chloride as eluant to yield the title compound as a colourless oil.

EXAMPLE 2l'

(2R,3R,5E)-2-hydroxy-3-methyl-5-hepten-1-aldehyde: flow-chart ②, formula VIa [Z=trans $CH_3-CH=CH-CH_2-$]

1.0 ml 1 N HCl are added to a solution of 1.7 g (7.9 mMol) of (2R,3R,5E)-2-[(1-ethoxyethyl)-1]-oxy-3-methyl-5-hepten-1-aldehyde in 20 ml tetrahydrofuran and the reaction mixture allowed to stand for 1½ hours at room temperature. The obtained solution is shaken with 100 ml water and 200 methylene chloride, the organic phase separated and washed again with 100 ml water. The aqueous phases are extracted with 200 ml methylene chloride, and the combined organic phases dried over sodium sulfate, filtered and evaporated to yield the title compound as a colourless oil. The product is used immediately for further reaction.

EXAMPLE 2n (1RS,2R,3R,5E)-1-cyano-2-hydroxy-3-methyl 1-methylamino-5-heptene: flow-chart 2, formula Va [Z=trans $CH_3-CH=CH-CH_2-$; $R_1=CH_3$]

0.52 g (7.9 mMol) KCN and 0.54 g (7.9 mMol) methylamine hydrochloride are added with stirring at 20° C. to 1.1 g (7.7 mMol) of (2R,3R,5E)-2-hydroxy-3-methyl-5-hepten-1-aldehyde dissolved in 50 ml methanol. After addition of 7.5 ml water the reaction mixture is stirred for a further two hours at room temperature and then concentrated to ½ volume on a rotary evaporator at a water-bath temperature of maximally 40° C. The obtained solution is shaken with 300 ml methylene chloride and 200 ml water and the separated organic phase is shaken with a further 100 ml water. The aqueous phases are extracted one after the other using 2×100 ml methylene chloride, the methylene chloride fractions are combined with the first organic extract, and the whole is dried over sodium sulfate, filtered through a $G_3$-frit and evaporated to yield the title compound as a diastereomeric mixture. This is used directly without further purification.

EXAMPLE 2n'

(1RS,2R,3R,5E)-2-[(1-ethoxyethyl)-1]-oxy-1-cyano-3-methyl-1-methylamino-5-heptene: flow-chart ②, formula Vb [Z=trans $CH_3-CH=CH-CH_2-$; $X_3=C_2H_5O-CH-(CH_3)-$; $R_1=CH_3$]

33.1 mg (4.81 mMol) KCN and 322 g (4.76 mMol) methylamine hydrochloride are added to a solution of 1.0 g (4.67 mMol) of (2R,3R,5E)-2-[(1-ethoxyethyl)-1]oxy-3-methyl-5-hepten-1-aldehyde in 40 ml methanol. After addition of 6 ml water the reaction mixture is stirred for 2 hours at room temperature, evaporated to 20 ml, and the residue shaken with 200 ml methylene chloride and 500 ml water. The aqueous phase is extracted with 50 ml methylene chloride, the combined organic phases dried over sodium sulfate, filtered and evaporated to yield the title compound as a diastereomeric mixture. This is used directly without further purification.

EXAMPLE 2l''

(1RS,2R,3R,5E)-1-cyano-2-hydroxy-3-methyl-1-methylamino-5-heptene: flow-chart ②, formula Va. [$R_1=CH_3$].

1.7 g (6.7 mMol) of (1RS,2R,3R,5E)-2-[(1-ethoxyethyl)-1]-oxy-1-cyano-3-methyl-1-methylamino-5-heptene dissolved in 20 ml dioxan are stirred for 20 hours at room temperature under a nitrogen atmosphere with 3 ml 2 N $H_2SO_4$. The reaction mixture is then poured onto 100 ml water and extracted with 200 ml methylene chloride. The aqueous phase is rendered alkaline by the addition of 6 ml 1 N NaOH, shaken 2× with 200 ml methylene chloride, dried over sodium sulfate, filtered and evaporated to yield the title compound. This is used for further reaction without additional purification.

EXAMPLE 2o (4R,5RS)-5-cyano-4-(hex-2E-en-5R-yl)-1-methyl-2-oxo-oxazoline: flow-chart ②, formula IV [Z=trans $CH_3-CH=CH-CH_2-$; $(X_2+X_3)=>C=O$; $R_1=CH_3$].

840 mg (5.2 mMol) carbonyldiimidazole are added to a solution of 630 mg (3.46 mMol) of (1RS,2R,3R,5E)-1-cyano-3-methyl-1-methylamino-2-hydroxy-5-heptene (c.f. examples 2n and 2l'') in 30 ml methylene chloride and the reaction mixture is stirred over-night at room temperature. The obtained solution is diluted with 100 ml methylene chloride and shaken with 50 ml water. The aqueous phase is extracted with 100 ml methylene chloride, the organic phase dried over sodium sulfate, filtered and evaporated. The residue is chromatographed on 110 g silica gel 60 using 1% methanolic methylene chloride as eluant to yield the title compound as a diastereomeric mixture.

EXAMPLE 2p'

(4R,5S)-4-(hex-2E-en-5R-yl)-1-methyl-2-oxo-oxazolin-5-carboxylic acid ethylester: flow-chart ②, formula IIIa¹ [(X₂+X₃)=>C=O; R₁=CH₃; R₂=C₂H₅-]

800 mg (2 mol equivalents) KOH are added to a solution of 600 mg (2.88 mMol) of (4R,5RS)-5-cyano-4-(hex-2E-en-5R-yl)-1-methyl-2-oxo-oxazoline in 95% ethanol and the mixture is stirred for 6 hours at room temperature. The obtained suspension is shaken with 300 ml methylene chloride and 100 ml water and the aqueous phase extracted with 100 ml methylene chloride. The combined organic phases are dried over sodium sulfate, filtered and evaporated. The residue is dissolved in 58 ml 95% ethanol and stirred with 2.9 ml 1 N NCl for 1½ hours at room temperature. The pH of the obtained solution is adjusted to 7 by the addition of 1 N sodium bicarbonate and extracted with methylene chloride. The combined organic phases are dried over sodium sulfate, filtered and evaporated to yield the title compound: rotation, $[\alpha]_D^{22} = +29.5°$ (c=1.0 in chloroform).

EXAMPLE 2q (4R,5S)-4-(2R-hexyl)-1-methyl-2-oxo-oxazolin-5-carboxylic acid ethyl ester: flow chart ②, formula IIIa² [(X₂+X₃)=>C=O; R₁=CH₃; R₂=C₂H₅]

23 mg 10% palladium/charcoal are added under a nitrogen atmosphere to a solution of 210 mg (0.82 mMol) of (4R,5S)-4-(hex-2-en-5R-yl)-1-methyl-2-oxo-oxazolin-5-carboxylic acid ethyl ester in 10 ml abs. ethanol. Hydrogenation is effected under a hydrogen atmosphere with a 3 hour reaction period. The obtained solution is filtered through talc, evaporated and chromatographed on 60 g silica gel 60 using 2% methanolic methylene chloride as eluant to yield the title compound as a colourless oil: rotation, $[\alpha]_D^{22} = +32.5°$ (c=0.93 in chloroform).

EXAMPLE 2r.1

(4R,5S)-4-(hex-2E-en-5R-yl)-1-methyl-2-oxo-oxazolin-5-carboxylic acid: flow-chart ②, formula IIIb¹ [(X₂+X₃)=>C=O; R₁=CH₃].

The (4R,5S)-4-(hex-2E-en-5R-yl)-1-methyl-2-oxo-oxazolin-5-carboxylic acid ethyl ester obtained in accordance with example 2p' is dissolved in 18 ml dioxan and stirred for 1 hour at room temperature with 50 ml 0.1 N NaOH. The obtained solution is adjusted to pH 2 by the addition of 1 N NCl, extracted 2× with 300 ml methylene chloride. The organic phases are dried over sodium sulfate, filtered and evaporated and the obtained residue re-crystallised from ether to yield the title compound in pure enantiomeric form: M.P. 81°-82° C.; rotation, $[\alpha]_D^{22} = +33.5°$ (c=1.0 in chloroform).

EXAMPLE 2r.2

(4R,5S)-4-(2R-hexyl)-1-methyl-2-oxo-oxazolin-5-carboxylic acid: flow-chart ②, formula IIIb² [(X₂+X₃)=>C=O; R₁=CH₃].

17 ml 0.1 N NaOH are added to a solution of 130 mg (0.50 mMol) of (4R,5S)-4-(2R-hexyl)-1-methyl-2-oxo-oxazolin-5-carboxylic acid ethyl ester in 7 ml dioxan and the reaction mixture stirred for 1 hour at room-temperature. The obtained solution is diluted with 150 ml methylene chloride, adjusted to pH 2 by the addition of 1 N HCl and the aqueous phase extracted with 100 ml methylene chloride. The combined organic phases are dried over sodium sulfate, filtered and evaporated. The title compound is obtained after re-crystallisation from ether: M.P.=109° C.

EXAMPLE 3

Proceeding analogously to example 2, but starting from (4R,5R)-4,5-dihydroxymethyl-2-phenyl-1,3-dioxolan in place of the corresponding (4S,5S)-isomer (c.f. example 2a), there are obtained:

(a1) at step p': (4S,5R)-4-(hex-2E-en-5S-yl)-1-methyl 2-oxo-oxazolin-5-carboxylic acid ethyl ester: rotation, $[\alpha]_D^{22} = -29.5°$ (c=1.0 in chloroform);

(b1) at step q': (4S,5R)-4-(2S-hexyl)-1-methyl-2-oxo-oxazolin-5-carboxylic acid ethyl ester: rotation, $[\alpha]_D^{22} = -32.5°$ (c=0.93 in chloroform);

(a2) at step r: (4S,5R)-4-(hex-2E-en-5S-yl)-1-methyl-2-oxo-oxazolin-5-carboxylic acid: rotation, $[\alpha]_D^{22} = -33.5°$ C. (c=1.0 in water);

(b2) at step r: (4S,5R)-4-(2S-hexyl)-1-methyl-2-oxo-oxazolin-5-carboxylic acid: M.P.=110° C.; and thence:

(a3) (2R,3S,4S,6E)-3-hydroxy-4-methyl-2-methylaminooct-6-enoic acid: M.P.=240°-241° C.; rotation, $[\alpha]_D^{22} = -13.0°$ (c=0.46 in water); and (b3) (2R,3S,4S)-3-hydroxy-4-methyl-2-methylaminooctanoic acid: M.P.=249°; rotation, $[\alpha]_D^{22} = -17°$ (c=0.44 in water).

EXAMPLE 4

Proceeding analogously to examples 2 and 3 but substituting ammonium chloride for methylamine hydrochloride at step n or n', there are obtained:

at step p¹:
(a1) (4R,5S)-4-(hex-2E-en-5R-yl)-2-oxo-oxazolin-5-carboxylic acid ethyl ester; and
(b1) (4S,5R)-4-(hex-2E-en-5S-yl)-2-oxo-oxazolin-5-carboxylic acid ethyl ester;

at step r:
(a2) (4R,5S)-4-(hex-2E-en-5R-yl)-2-oxo-oxazolin-5-carboxylic acid; and
(b2) (4S,5R)-4-(hex-2E-en-5S-yl)-2-oxo-oxazolin-5-carboxylic acid;
and thence:

(a3) (2S,3R,4R,6E)-3-hydroxy-4-methyl-2-amino-oct-6-enoic acid: M.P.=188°-192° C.; rotation, $[\alpha]_D^{20} = +22.6°$ C. (c=0.265 in 0.1 N HCl); and (b3) (2R,3S,4S,6E)-3-hydroxy-4-methyl-2-amino-oct-6-enoic acid: M.P. 189°-191° C., rotation, $[\alpha]_D^{20} = 22.6°$ (c=0.265 in 0.1 N HCl).

EXAMPLE 5

Synthesis of (2S,3R,4R,6Z)-3-hydroxy-4-methyl-2-methylamino-oct-6-enoic acid

The above identified compound is produced analogously to example 2, substituting procedures 4j, 4r and 4 below for example 2j, 2r and 2.1 respectively:

5j: (4R)-4-(hex-2Z-en-5R-yl)-2-dimethyl-1,3-dioxolan:

40 ml phenyl-lithium are added at room temperature with stirring within 12 mins. to a suspension of 30.0 g triphenylphosphonium bromide in 270 ml abs. tetrahydrofuran and 70 ml diethyl-ether, whereby the temperature rises to 27° C. The obtained red-coloured suspension is stirred for 1½ hours at room temperature, and a solution of 6.92 g (40.2 mMol) of (3R)-3-[4R-(2-dimethyl)-1,3-dioxolanyl]butyraldehyde in 130 dimethyl-ether is then added at room temperature, whereupon the colour of the reaction medium changes from red to orange. After stirring for a further 5 hours at room temperature the reaction mixture is poured onto 1000 ml water and extracted 2× with 750 ml methylene chloride. The combined organic phases are dried over sodium sulfate, filtered through a glass frit and evaporated under low vacuum. The obtained precipitate is removed by filtration and the concentrated solution chromatographed on 250 g silica gel 60 using 1% methanol in methylene chloride as eluant, to yield the title compound, exhibiting the low IR- absorption at 970 cm$^{-1}$ characteristic of a cis- double bond.

5r:  (4R,5S)-4-(hex-2Z-en-5R-yl)-1-methyl-2-oxo-oxazolin-5-carboxylic acid:

185 g (0.81 mMol) or (4R,5S)-4-(hex-2Z-en-5R-yl)-1-methyl-2-oxo-oxazolin-5-carboxylic acid ethyl ester are added to 25 ml 0.1 N NaOH in 9 ml dioxane and the reaction mixture stirred for 2 hours at room temperature. The reaction product is poured onto 100 ml water and adjusted to pH 2 by the addition of 1 N HCl. The acid aqueous phase is extracted 2× with 150 ml methylenechloride, and the organic phase dried over sodium sulfate, filtered and evaporated to yield the title compound.

5:  (2S,3R,4R,6Z)-3-hydroxy-4-methyl-2-methylaminooct-6-enoic acid:

67 mg (0.3 mMol) of (4R,5S)-4-(hex-2Z-en-5R-yl)-1-methyl-2-oxo-oxazolin-5-carboxylic acid are heated at 70° C. for 8 hours in 2.0 ml 2 N KOH. The obtained reaction mixture is cooled, adjusted to pH 6 by the addition of 1 N HCl and extracted 2× with 50 ml dichloromethane to recover non-reacted starting material. The aqueous solution is evaporated to dryness on a rotary evaporator and the crystalline residue taken up in 50 ml methanol. The undissolved portion is removed by filtration, the methanolic solution concentrated to 10 ml and chromatographed on 40 g Sephadex LH 20 using methanol as eluant. The eluate is collected in 8 ml fractions, and the title compound recovered by crystallisation from fractions 9 through 15 by the addition of 3 drops 1 N HCl (pH 5): M.P. 228°–233° C.; rotation, $[\alpha]_D^{22} = +8°$ C. (c=0.38 in water).

EXAMPLE 6

Proceeding analogously to example 4, but starting from (4R,5R)-4,5-dihydroxymethyl-2-phenyl-1,3-dioxolan in place of the corresponding (4S,5S)-isomer of example 2a, there are obtained:

(a1)  (4S,5R)-4-(hex-2Z-en-5S-yl)-1-methyl-2-oxo-oxazolin-5-carboxylic acid ethyl ester;

(a2)  (4S,5R)-4-(hex-2Z-en-5S-yl)-1-methyl-2-oxo-oxazolin-5-carboxylic acid; and (a3)  (2R,3S,4S,6Z)-3-hydroxy-4-methyl-2-methylaminooct-6-enoic acid; rotation, $[\alpha]_D^{22} = -8°$ (c=0.42 in water).

EXAMPLE 7

Production of (4R,5S)-4-(hex-3E-en-5R-yl)-1,2-trimethyl-oxazolin-5-carboxylic acid [formula III: $X_1$=OH; $(X_2+X_3)=>C(CH_3)_2$; $R_1$=CH$_3$; x-y=trans -CH=CH-].

201 mg (1 mMol) of (2S,3R,4R,6E)-3-hydroxy-4-methyl-2-methylamino-oct-6-enoic acid, suspended in 80 ml anhydrous acetone are heated under re-flux for 48 hours until a clear solution is obtained. The acetone is completely evaporated under vacuum and the remaining oil taken up in 100 ml methylene chloride, washed with 30 ml water, dried over sodium sulfate and evaporated at room temperature. The obtained title compound may be used directly for synthetic purposes, e.g. for peptide synthesis, without further purification.

EXAMPLE 8

Production of (2S,3R,4R,6E)-2-(N-t.-butyloxy-carbonyl)-methylamino-3-hydroxy-4-methyl-oct-6-enoic acid [formula III: $X_1$=OH; $X_2$=(CH$_3$)$_3$CO-; $X_3$=H; $R_1$=CH$_3$; -x-y-=trans -CH=CH-].

201 mg (1 mMol) of (2S,3R,4R,6E)-3-hydroxy-4-methyl-2-methylamino-oct-6-enoic acid are dissolved in a solution comprising 2.2 ml 1 N NaOH and 0.33 g (1.5 mMol) bis-(t.-butyl)-dicarbonate in 5 ml dioxan and the reaction mixture stirred for 2 days at room temperature. The obtained solution is taken up in 200 ml methylene chloride, the aqueous phase adjusted to pH 3 by the addition of 2 N H$_2$SO$_4$ and extracted. The organic phase is washed 2× with 30 ml water, dried over sodium sulfate, filtered and evaporated. The obtained colourless oil is chromatographed on 15 g silica gel 60 using 2% methanolic methylene chloride as eluant to yield the title compound: rotation, $[\alpha]_D^{20} = +7.2°$ (±2°) (c=1.0 in chloroform). The compound may be employed directly for synthetic purposes, e.g. for peptide synthesis.

EXAMPLE 9

Proceeding analogously to examples 7 and 8 but starting from the corresponding (2R,3S,4S)-octenoic acid isomer as starting material, there are obtained:

(a1)  (4S,5R)-4-(hex-2E-en-5S-yl)-1,2-trimethyl-oxazolin-5-carboxylic acid; and (a2)  (2R,3S,4S,6E)-2-(N-t.-butyloxy-carbonyl)-methylamino-3-hydroxy-4-methyl-oct-6-enoic acid: rotation, $[\alpha]_D^{20} = -7.2°$ (±2°) (c=1.0 in chloroform).

EXAMPLE 10

Proceeding analogously to examples 7 and 8 but starting from (2S,3R,4R,6E)- and (2R,3S,4S,6E)-3-hydroxy-4-methyl-2-amino-oct-6-enoic acid there are obtained:

(a) (2S,3R,4R,6E)-2-(N-t.-butyloxy-carbonyl)-amino-3-hydroxy-4-methyl-oct-6-enoic acid; rotation $[\alpha]_D^{20} = +2.2$ (c=1.0 in chloroform); and (b) (2R,3S,4S,6E)-2-(N-t.-butyloxy-carbonyl)-amino-3-hydroxy-4-methyl-oct-6-enoic acid; rotation, $[\alpha]_D^{20} = -2.2$ (c=1.0 in chloroform).

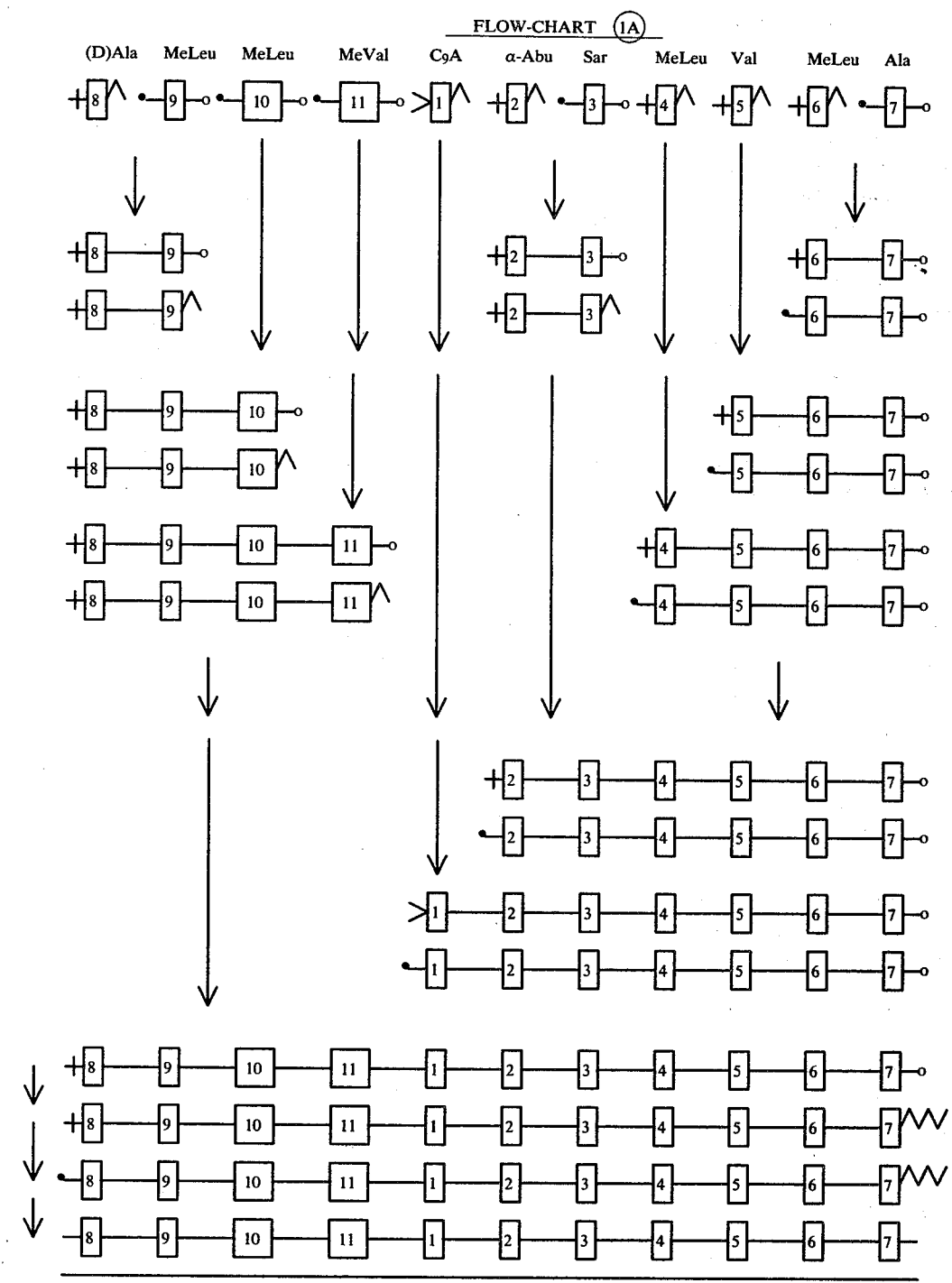
Cyclosporin A
KEY:
• —— = H
∧ = OH
+ = COOC(CH₃)₃
> = (2N, 3O) >C(CH₃)₂
—o = —OCH₂C₆H₅
∿∿ = —NHNH₂

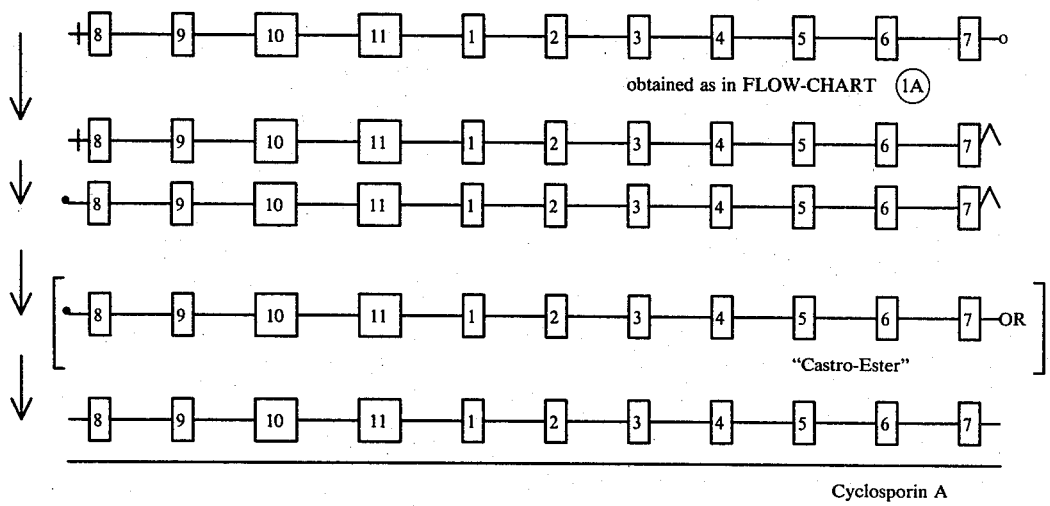
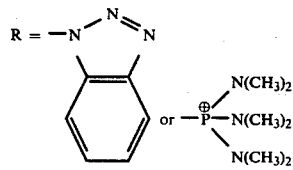
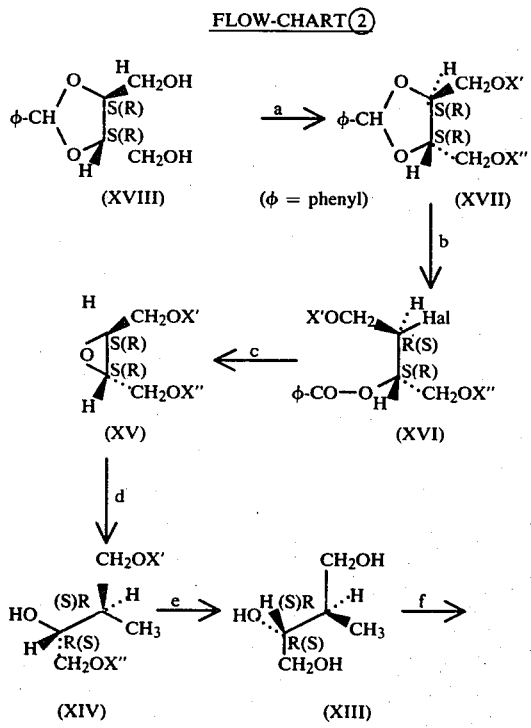
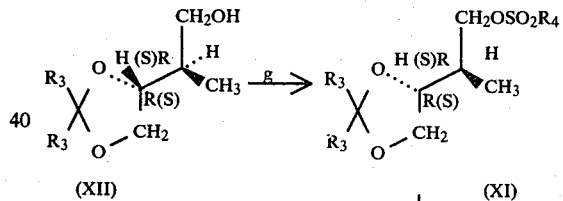
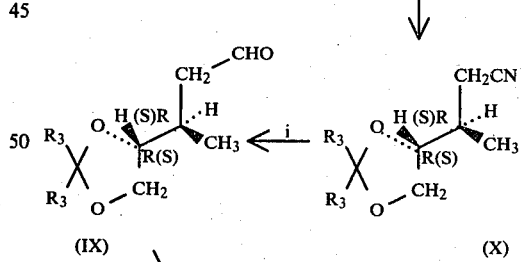
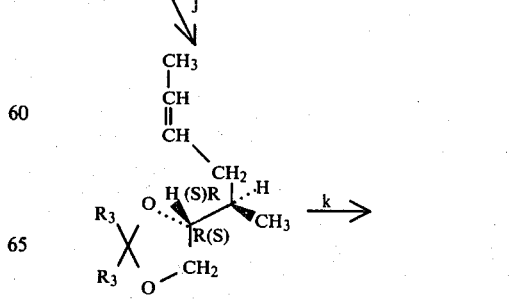

-continued
FLOW-CHART 2
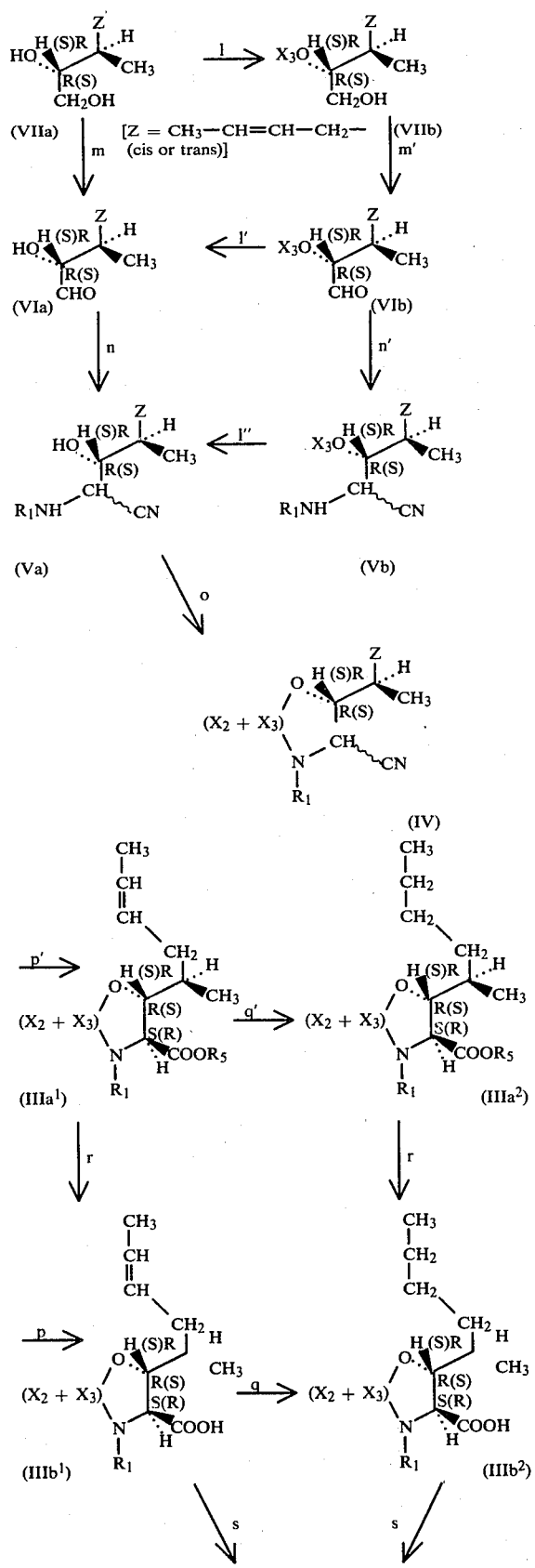
-continued
FLOW-CHART 2
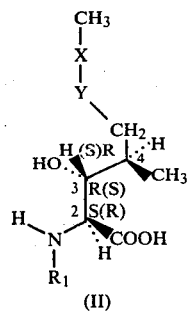
(II)
We claim:
1. Process for the production of a cyclosporin of formula I,
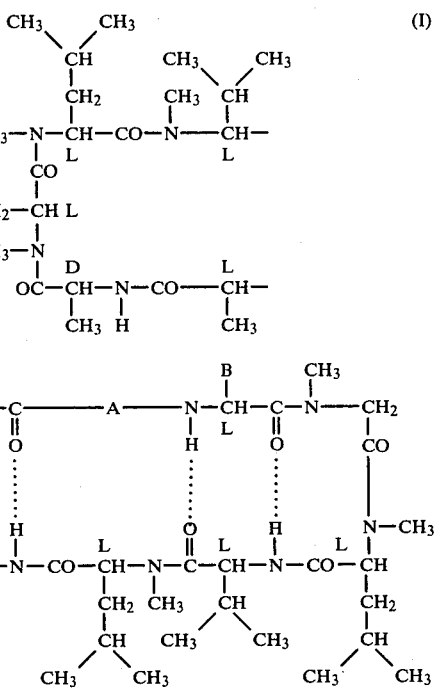
wherein A is a residue of formula Ia,
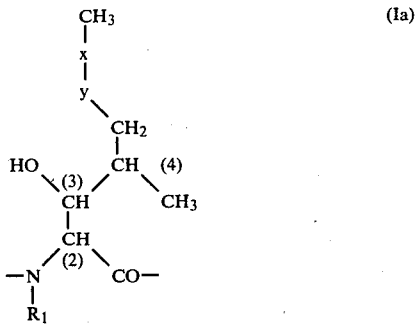
wherein $R_1$ is hydrogen or methyl and -x-y- is -$CH_2$-$CH_2$- or -CH=CH- and the positions 2, 3 and 4 have the configuration S,R and R or R,S and S respectively, and B is ethyl, 1-hydroxyethyl, isopropyl or n-propyl, which process comprises (a) removing the O-protecting group(s) from a cyclosporin of formula I in O-protected form;
(b) cyclising a straight-chain endecapeptide having the sequence indicated in formula I, commencing with H-(D)-Ala- as N-terminal and terminating with -Ala-OH as C-terminal, in unprotected or O-protected form and, when required, carrying out process step (a); and, when desired,
(c) hydrogenating a cyclosporin of formula I thus obtained wherein -x-y- is -CH=CH- to obtain the corresponding cyclosporin wherein -x-y- is -CH$_2$-CH$_2$-.

2. A process according to claim 1, in which the straight-chained endecapeptide, in free -N and carboxy-activated form is cyclized to produce the cyclosporin of formula (I).

3. A process according to claim 2, in which the carboxy-activated form is a carbonyl azide.

4. A process according to claim 3, in which the carbonyl azide is cyclized by the addition of a base at −20° to 0° C.

5. A process according to claim 4, in which the base is triethylamine or ethyldiisopropylamine.

6. A process according to claim 2, in which the carboxy-activated form is a Castro-ester.

7. A process according to claim 6, in which preparation of the Castro-ester and cyclisation of the ester are carried out concurrently in the presence of a base, at a temperature of from −20° to 30° C. in an inert solvent.

8. A process according to claim 7, in which the base is triethylamine or N-methylmorpholine and the solvent is chloroform or methylene chloride.

9. A process according to claim 1 for the production of a cyclosporin of formula (I), in which the residue A is an unprotected or O-protected C$_9$-amino acid of formula (Ia) occupying position 1 and the remaining amino acid residues of the of the molecule are numbered from 1 clockwise and in sequence, comprising the steps of:
  1. Preparation of a tetrapeptide having the sequence 4 through 7, commencing with 7 and proceeding by successive linkage of the residues 6, 5 and 4 to the N-terminal;
  2. Preparation of a dipeptide having the unprotected or O-protected sequence 2-3 and linkage of this dipeptide to the N-terminal of the tetrapeptide obtained in step 1, to obtain a hexapeptide having the sequence 2 through 7;
  3. Linkage of the C$_9$-amino acid to the N-terminal of the hexapeptide obtained in step 2, to obtain a heptapeptide having the sequence 1 through 7;
  4. Preparation of a tetrapeptide having the sequence 8 through 11 and linkage of this tetrapeptide to the N-terminal of the heptapeptide obtained in step 3 to obtain a linear endecapeptide having the sequence 8 through 7;
  5. Cyclisation of the straight-chain endecapeptide obtained in step 4 in unprotected or O-protected form and, when required removing the O-protecting groups to obtain a cyclosporin wherein -X-Y- is -CH=CH-; and, when desired;
  6. Hydrogenation of the cyclosporin obtained in step 5 to obtain the corresponding cyclosporin wherein -X-Y- is -CH$_2$-CH$_2$-.

10. A process according to claim 9, in which the cyclosporin obtained is cyclosporin A, B, C, D or G or a corresponding dihydro derivative thereof.

11. A process according to claim 9, in which the straight-chained endecapeptide, in free —N and carboxy-activated form is cyclized to produce the cyclosporin of formula (I).

12. A process according to claim 11, in which the carboxy-activated form is a carbonyl azide.

13. A process according to claim 12, in which the carbonyl azide is cyclized by the addition of a base at −20° to 0° C.

14. A process according to claim 13, in which the base is triethylamine or ethyldiisopropylamine.

15. A process according to claim 11, in which the carboxy-activated form is a Castro-ester.

16. A process according to claim 11, in which preparation of the Castro-ester and cyclisation of the ester are carried out concurrently in the presence of a base, at a temperature of from −20° to 30° C. in an inert solvent.

17. A process according to claim 16, in which the base is triethylamine or N-methylmorpholine and the solvent is chloroform or methylene chloride.

* * * * *